(12) United States Patent
Shibutani et al.

(10) Patent No.: US 6,217,172 B1
(45) Date of Patent: Apr. 17, 2001

(54) OPHTHALMOLOGIC MEASURING SYSTEM

(75) Inventors: Masahiro Shibutani; Satoru Niimura, both of Tokyo-to (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 0 days.

(21) Appl. No.: 09/516,366

(22) Filed: Mar. 1, 2000

(30) Foreign Application Priority Data

Mar. 17, 1999 (JP) .................................................. 11-072632

(51) Int. Cl.⁷ ........................................................ A61B 3/10
(52) U.S. Cl. ............................ 351/204; 351/210; 351/221
(58) Field of Search .................................... 351/204, 209, 351/210, 211, 212, 221; 359/630, 631, 632, 633

(56) References Cited

U.S. PATENT DOCUMENTS 5,699,194 * 12/1997 Takahashi ............................. 359/633
5,726,807 * 3/1998 Nakaoka et al. ...................... 359/631
5,768,024 * 6/1998 Takahashi ............................. 359/631

* cited by examiner

Primary Examiner—George Manuel
(74) Attorney, Agent, or Firm—Nields & Lemack

(57) ABSTRACT

An ophthalmologic measuring system, comprising a light source unit 4 for emitting an illuminating light beam for illuminating a fundus of each of both eyes of a person under measurement, a projection optical system 1 for projecting the illuminating light beam from said light source unit to the fundus of each of the eyes of the person under measurement, a photodetection optical system 2 including a light blocking member which blocking a part of a reflection light beam coming from the fundus of the eye of the person under measurement and is arranged in an optical path and at approximately conjugate position to a pupil of the eye under measurement so that change occurs in light amount distribution depending on ocular refractive power, a photodetection unit 9 arranged at approximately conjugate position to the pupil of the eye under measurement and receives photodetection light beam from said photodetection optical system, a storage unit for storing a photodetection signal of said photodetection unit, a control arithmetic unit 13 for obtaining at least one of interpupillary distances, ocular refractive powers and pupil diameters of the eye under measurement based on the photodetection signal of the photodetection unit, and a display unit 14 for displaying an anterior ocular segment image of the eye under measurement during measurement period and for displaying over time and at real time the data of interpupillary distance, ocular refractive power and pupil diameter of the eye under measurement, which are results of measurement during measurement period.

7 Claims, 23 Drawing Sheets

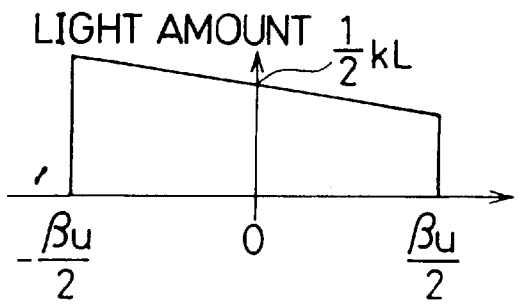
FIG.8
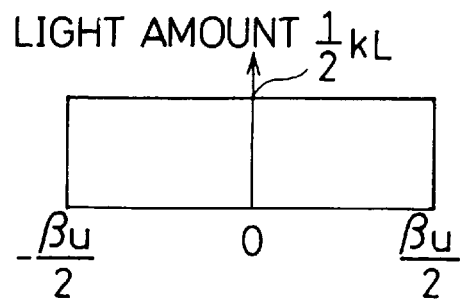
FIG.9
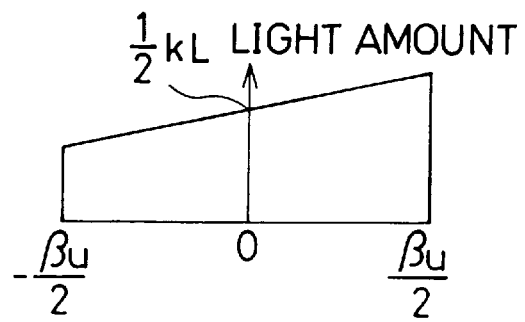
FIG.10
FIG.11
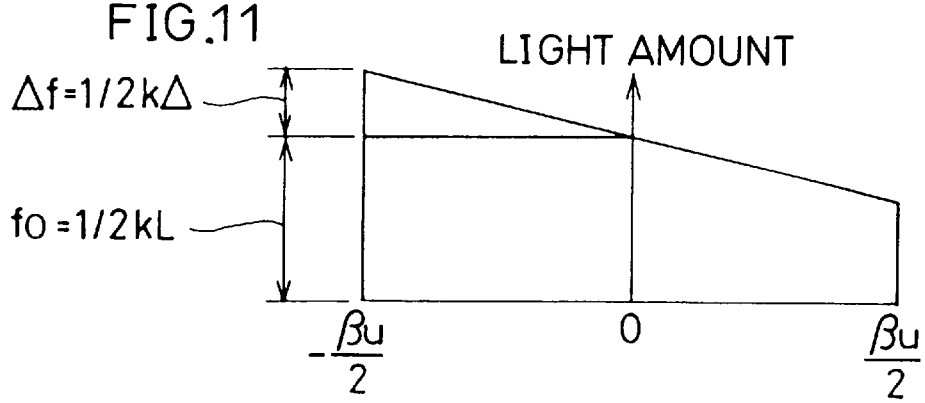

FIG.12A  FIG.12B  FIG.12C
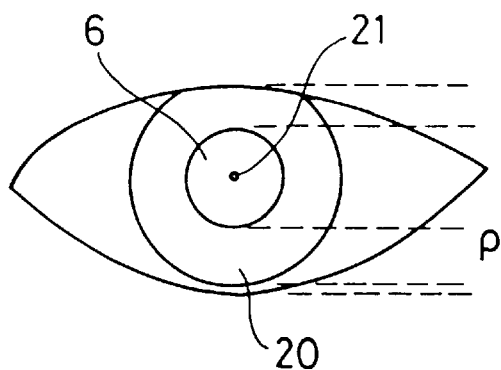 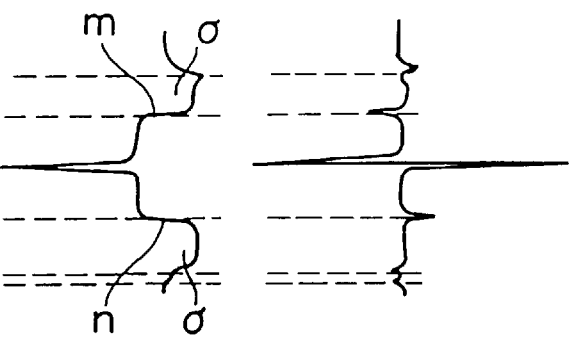
FIG.13A  FIG.13B  FIG.13C
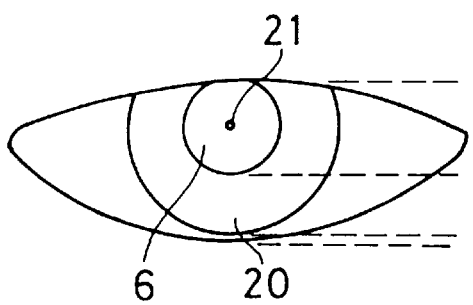 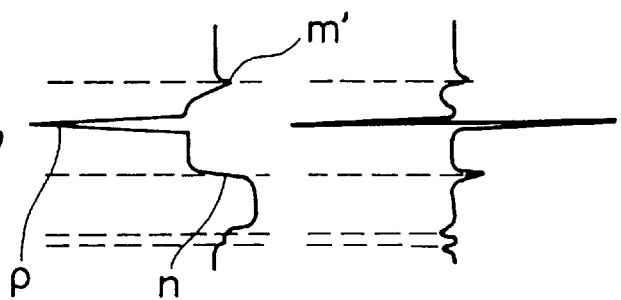

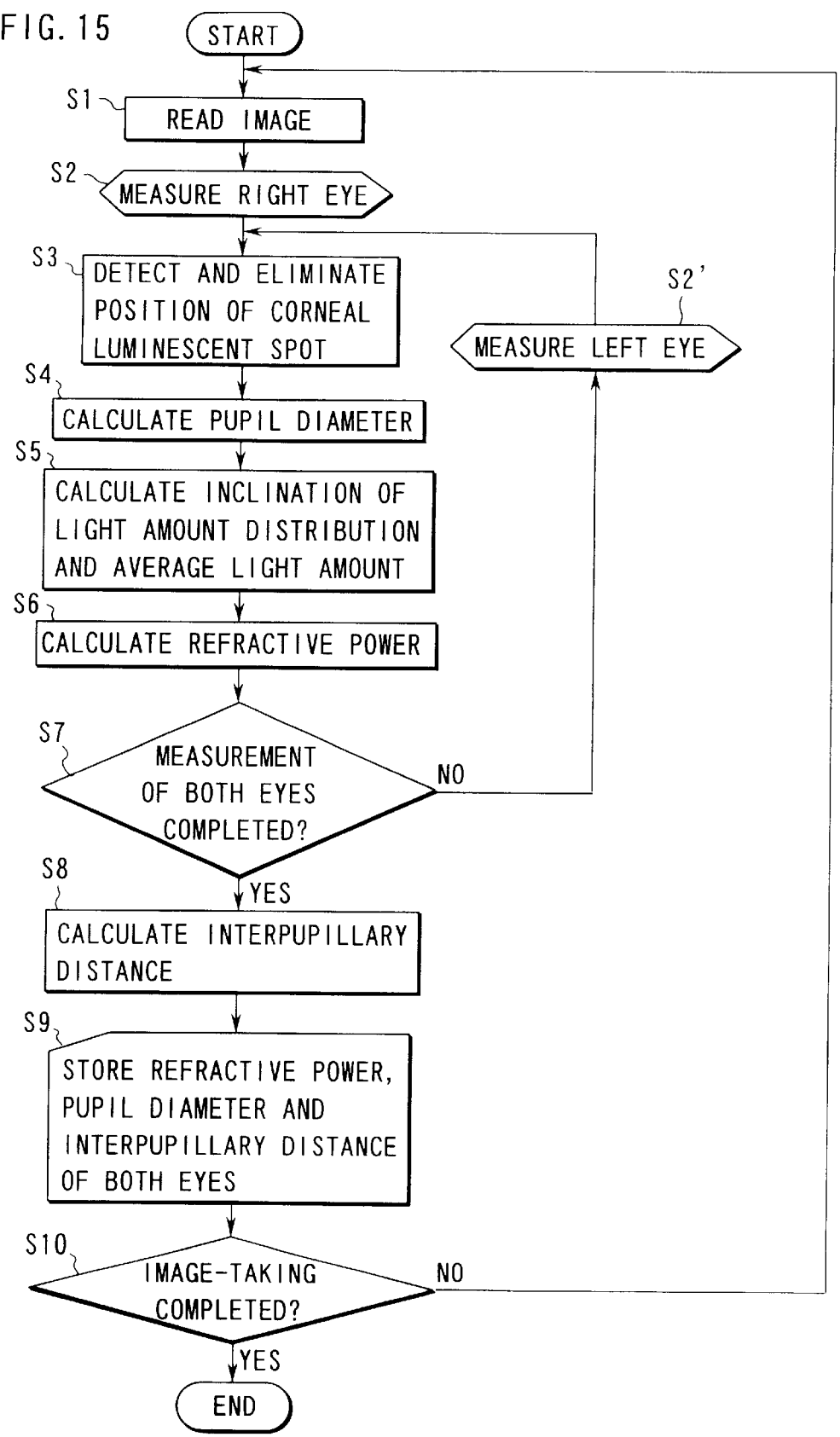

RELATION BETWEEN STIMULATION AND 3 FACTORS OF NEAR VISION: WHEN TARGET IS INSTANTANEOUSLY CHANGED: FAR → NEAR

OPHTHALMOLOGIC MEASURING SYSTEM

BACKGROUND OF THE INVENTION

The present invention relates to an ophthalmologic measuring system, and in particular to an ophthalmologic measuring instrument for determining changes over time of an eye under measurement in the state of natural vision, or for measuring changes of data such as interpupillary distance, ocular refractive power and pupil diameter of an eye under measurement and for displaying the data at real time, and also capable to display the data again after measurement.

In the past, no system has been proposed, which can continuously obtain data of ocular refractive power, interpupillary distance and pupil diameter before and after change of position of a target and can display the data in synchronization with the changes of an anterior ocular segment.

In recent years, there have been strong demands on a system, which can measure, continuously and at real time, the change of data such as ocular refractive powers, interpupillary distances and pupil diameters before and after the change of target position.

In Japanese Patent Application Heisei 10-54305, the present applicant has proposed an ophthalmologic measuring system, which is suitable for the purpose of obtaining data such as ocular refractive powers, interpupillary distances and pupil diameters before and after change of target position when position of the target is changed.

However, in the ophthalmologic measuring system described in the above patent application, there is no description on a system, which can obtain data such as ocular refractive powers, interpupillary distances and pupil diameters when the position of the target is changed and can display the data in synchronization with the changes of anterior ocular segment. In this respect, the system does not satisfy the requirements to measure the data of the anterior ocular segment continuously and at real time.

SUMMARY OF THE INVENTION

It is an object of the present invention to provide an ophthalmologic measuring system which can obtain data such as ocular refractive power, interpupillary distance and pupil diameter and data relating to anterior ocular segment at real time when position of the target is changed.

The ophthalmologic measuring system according to the present invention comprises a light source unit for emitting an illuminating light beam for illuminating a fundus of each of both eyes of a person under measurement, a projection optical system for projecting the illuminating light beam from the light source unit to the fundus of each of the eyes of the person under measurement, a photodetection optical system including a light blocking member which blocks a part of a reflection light beam coming from the fundus of an eye of the person under measurement and is arranged in an optical path and at approximately conjugate position to a pupil of the eye under measurement so that change occurs in light amount distribution depending on ocular refractive power, a photodetection unit arranged at approximately conjugate position to the pupil of the eye under measurement and receives photodetection light beam from the photodetection optical system, a storage unit for storing a photodetection signal of the photodetection unit, a control arithmetic unit for obtaining at least one of interpupillary distances, ocular refractive powers and pupil diameters of the eye under measurement based on the photodetection signal of the photodetection unit, and a display unit for displaying an anterior ocular segment image of the eye under measurement during measurement period and for displaying over time and at real time the data of interpupillary distance, ocular refractive power and pupil diameter of the eye under measurement, which are results of measurement during measurement period. The present invention provides an ophthalmologic measuring system as described above, wherein said system further comprises a target system for showing a target to the person under measurement by changing the target position from a first target position to a second target position different from said first target position in response to operation by a measuring person, wherein the control arithmetic unit determines at least one of interpupillary distances, ocular refractive powers and pupil diameters of the eye under measurement before and after change of the target positions based on the photodetection signals of the photodetection unit obtained before and after change of the target position by the target system. Further, the present invention provides an ophthalmologic measuring system as described above, wherein the system comprises a storage unit for storing an anterior ocular segment signal from the photodetection unit, and an anterior ocular segment image of the eye under measurement is displayed on the display unit with delay of time as required for arithmetic processing at the control arithmetic unit based on the signal stored in the storage unit, and the anterior ocular segment image when the target position is changed and results of the measurement are displayed at real time. Also, the present invention provides an ophthalmologic measuring system, which comprises a light source unit for emitting an illuminating light beam for illuminating a fundus of each of both eyes of a person under measurement, a projection optical system for projecting the illuminating light beam from the light source unit to fundus of each of the eyes of the person under measurement, a photodetection optical system including a light blocking member which blocks a part of the reflection light beam coming from fundus of each of the eye of the person under measurement and is arranged in an optical path and at approximately conjugate position to the pupil of the eye under measurement so that change occurs in light amount distribution depending on ocular refractive power, a photodetection unit arranged at approximately conjugate position to a pupil of the eye under measurement and receives photodetection light beam from the photodetection optical system, a storage unit for storing a photodetection signal of the photodetection unit, a target system for indicating a target to the person under measurement by changing target position from a first target position to a second target position different from the first target position, a control arithmetic unit for obtaining interpupillary distances, ocular refractive powers and pupil diameters of the eye under measurement before and after change of the target position based on the photodetection signals of the photodetection unit obtained before and after change of the target position by the target system, a storage unit for storing an anterior ocular segment signal of the photodetection unit and results of calculation by the control arithmetic unit in association with movement of the target by the target system, and a display unit for displaying an anterior ocular segment of the photodetection unit and the results of calculation by the control arithmetic unit in association with the movement of the target by the target system based on the anterior ocular segment signal stored in the storage unit and the results of the calculation. Further, the present invention provides an ophthalmologic measuring system as described above, wherein the display unit aligns and displays pupil images in association with the movement of the target by the target system so that movement of pupils of the eye under measurement on the photodetection unit can be sequentially identified. Also, the present invention provides an ophthalmologic measuring system as described above, wherein pupil images are partially overlapped each other or are displayed in different colors. Further, the present invention provides an ophthalmologic measuring system as described above, wherein the display unit is designed in such manner that movement of the target system can be visually identified.

BRIEF DESCRIPTION OF THE DRAWINGS

FIG. 8 shows a status of light amount distribution on a photodetection surface corresponding to diopter value;

FIG. 9 shows a status of light amount distribution on a photodetection surface corresponding to diopter value;

FIG. 10 shows a status of light amount distribution on a photodetection surface corresponding to diopter value;

FIG. 11 is a diagram to explain a case where diopter value is obtained from the condition of light amount distribution;

FIG. 12(A) is a drawing to show a normal eye condition, FIG. 12(B) is a diagram showing light amount distribution under the above condition, and FIG. 12(C) is a diagram showing light amount change rate under the same condition;

FIG. 13(A) is a drawing to show a blinking eye, FIG. 13(B) is a diagram showing light amount distribution under the same condition, and FIG. 13(C) is a diagram showing light amount change rate under the same condition;

FIG. 15 is a flow chart showing a measuring method in the above embodiment;

DETAILED DESCRIPTION OF THE PREFERRED EMBODIMENTS

Figure 1:
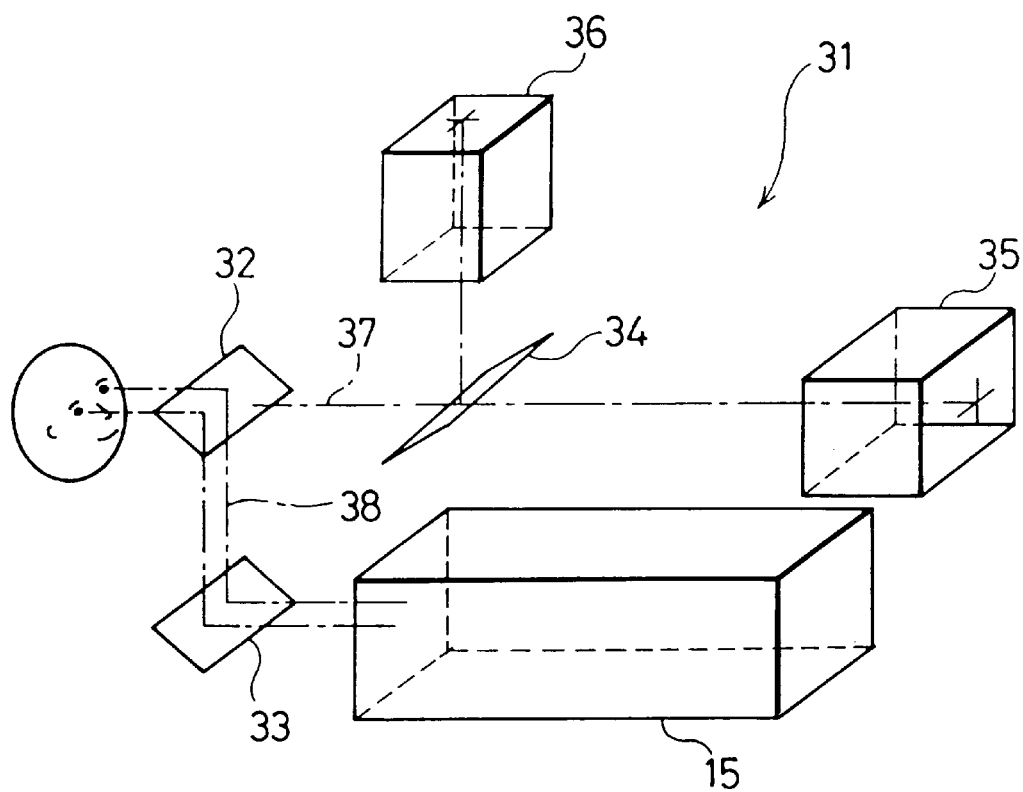
FIG. 1 is a schematical drawing to show general arrangement of an embodiment of the present invention.

In the following, description will be given on embodiments of the present invention referring to the drawings.

First, a first embodiment will be described referring to FIG. 1 and FIG. 2.

In FIG. 1, reference numeral 15 indicates a measuring optical system using infrared light, and 31 represents a target system using visible light.

An optical axis of the measuring optical system 15 and an optical axis of the target system 31 are split by a dichroic mirror 32, which is arranged at a position opposite to a person under measurement. The target system 31 is disposed on a transmission light optical axis 37 of the dichroic mirror 32, and the measuring optical system 15 is arranged on a reflection light optical axis 38 of the dichroic mirror 32.

The transmission light optical axis 37 is further split by a half-mirror 34. A first gaze target 35 used for long distance measurement is arranged on a transmission light optical axis of the half-mirror 34, and a second gaze target 36 for near distance measurement is arranged on a reflection light optical axis of the half-mirror 34. The first gaze target 35 and the second gaze target 36 are provided respectively with a gaze target illuminating source (not shown), which emits light beam in visible light range, and the gaze target illuminating sources can be selectively turned on.

Description will be given now on the measuring optical system 15 referring to FIG. 2. Reference numeral 1 represents a projecting optical system for projecting a light source image to a fundus 7 of an eye under measurement 3. Reference numeral 2 represents a photodetection optical system for receiving a reflection light beam 10 reflected by the fundus 7. The projecting optical system 1 and the photodetection optical system 2 are arranged at positions opposite to the eye under measurement 3.

The projecting optical system 1 comprises a light source 4 for emitting a projecting light beam 11 of infrared range, and a half-mirror 5 and a mirror 33 for reflecting the projecting light beam 11 toward the eye under measurement 3. The projecting optical system 2 projects the projecting light beam 11 from the light source 4 to pass through a pupil 6 and to form an image of the light source 4 on the fundus 7. It is designed in such manner that the image of the light source 4 is formed on the fundus 7 when ocular refractive power of the eye under measurement 3 has a standard diopter value (standard ocular refractive power).

The photodetection optical system 2 comprises a light blocking member 12 placed at a position opposite to the eye under measurement 3, an image-forming lens 8, and a photodetection element 9. The reflection light beam 10 coming from the fundus 7 passes through the half-mirror 5 and is guided toward the photodetection element 9. The photodetection element 9 comprises an area CCD and an image pickup tube, or an aggregate of these two components, and a photodetection surface 9a of the photodetection element 9 is arranged at conjugate position to the pupil 6 of the eye under measurement 3 with respect to the image-forming lens 8.

The light blocking member 12 has an edge and it is positioned in such manner that a ridge line of the edge is aligned with an optical axis O of the photodetection optical system 2 and a part of the reflection light beam 10 on one side of the optical axis O is blocked and it is placed at conjugate position to the light source 4 with respect to the half-mirror 5. It is designed in such manner that an image of the fundus 7 is focused on the light blocking member 12 when ocular refractive power of the eye under measurement 3 is at the standard diopter value.

Figure 2:
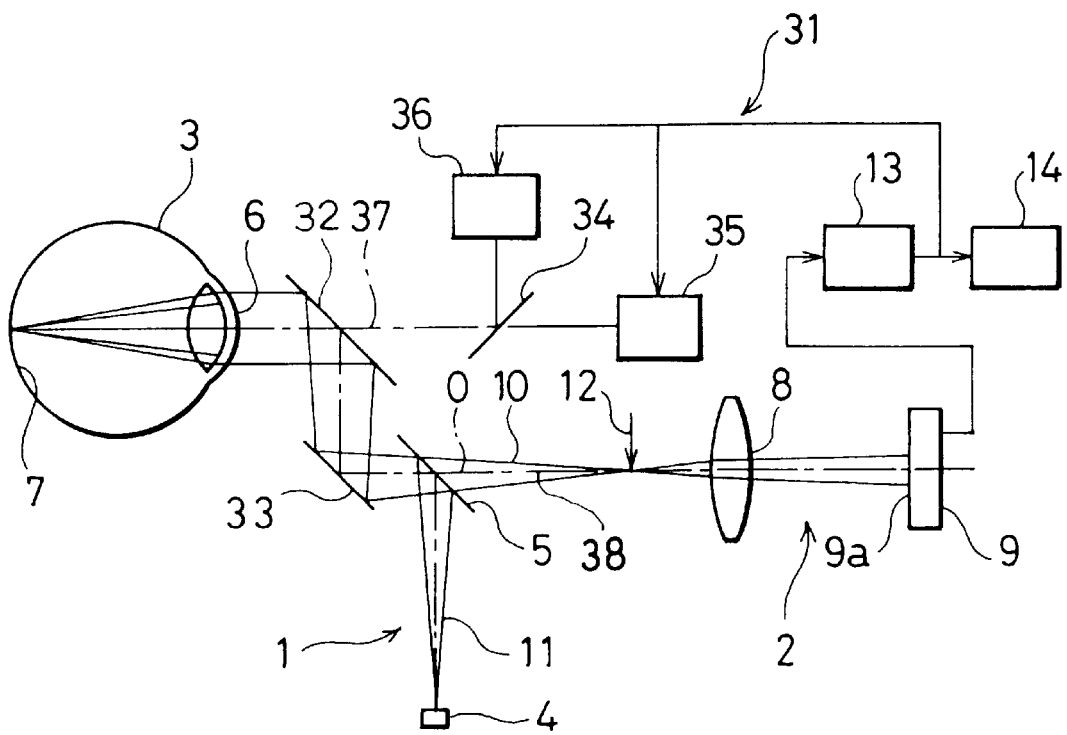
FIG. 2 is a schematical block diagram of the embodiment of the present invention.

In FIG. 2, reference numeral 13 represents an arithmetic unit, to which the photodetection element 9, the first gaze target 35, and the second gaze target 36 are connected.

The arithmetic unit 13 controls on-off operation of the first gaze target 35 and the second gaze target 36. Also, it calculates diopter value, pupil diameter and interpupillary distance from photodetection status of the photodetection element 9 and from light amount distribution, and the result is outputted to a display unit 14.

Measurement of ocular refractive power is measured under the condition where the first gaze target 35 and the second gaze target 36 of the target system 31 are collimated by the person under measurement.

Description will be given now on the measuring principle of 3 factors of ocular refractive power, pupil diameter and interpupillary distance in the ophthalmologic measuring system with the above arrangement.

Figure 3A:
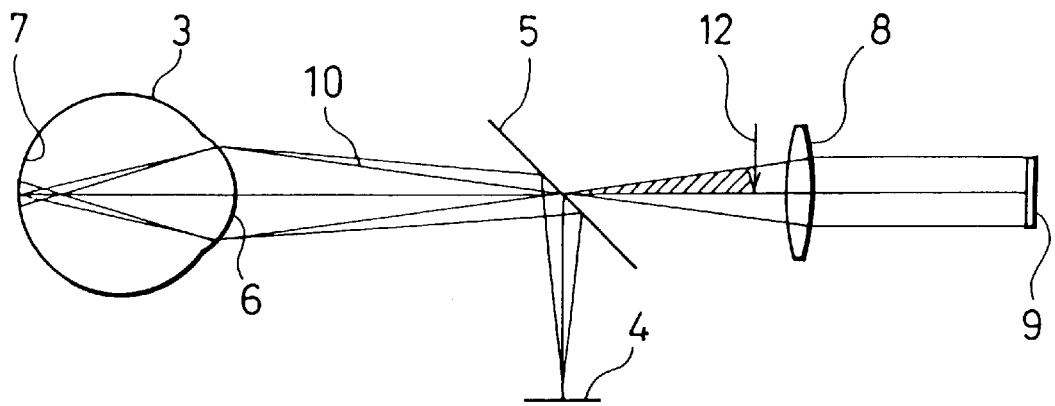
FIG. 3(A), FIG. 3(B) and FIG. 3(C) each represents a drawing to show difference of the conditions of light beam due to difference of diopter value of an eye under measurement.

As shown in FIG. 3(A), in case the diopter value of the eye under measurement 3 is negative compared with a standard diopter value selected, the image of the light source 4 is formed at a point before the fundus 7. If we observe the reflection light beam 10 reflected at one point on the optical axis in a space over the fundus 7 projected by the light beam, the reflection light beam 10 is converged at a point in front of the light blocking member 12, i.e. at a point closer to the eye under measurement 3, and upper half (shaded portion) of the light beam projected to the photodetection element 9 through the image-forming lens 8 is blocked by the light blocking member 12.

Figure 3B:
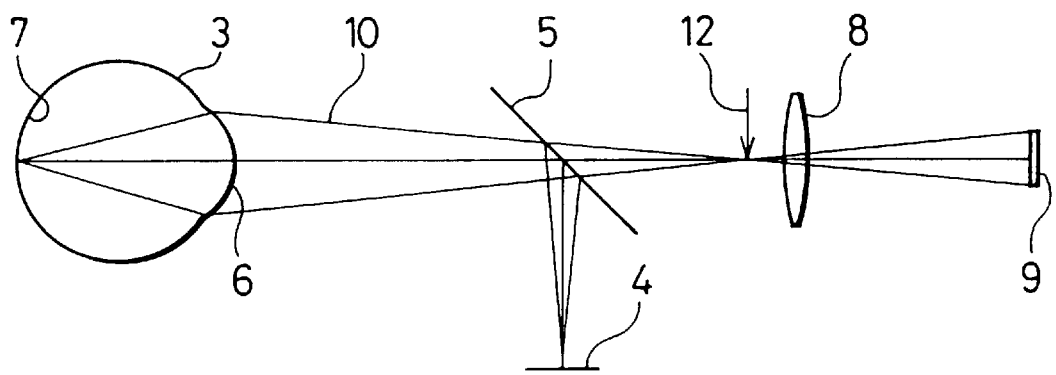

On the other hand, as shown in FIG. 3(B), when diopter value of the eye under measurement is the standard diopter value, the reflection light beam 10 is converged on the light blocking member 12, and the reflection light beam 10 is not blocked by the light blocking member 12.

Figure 3C:
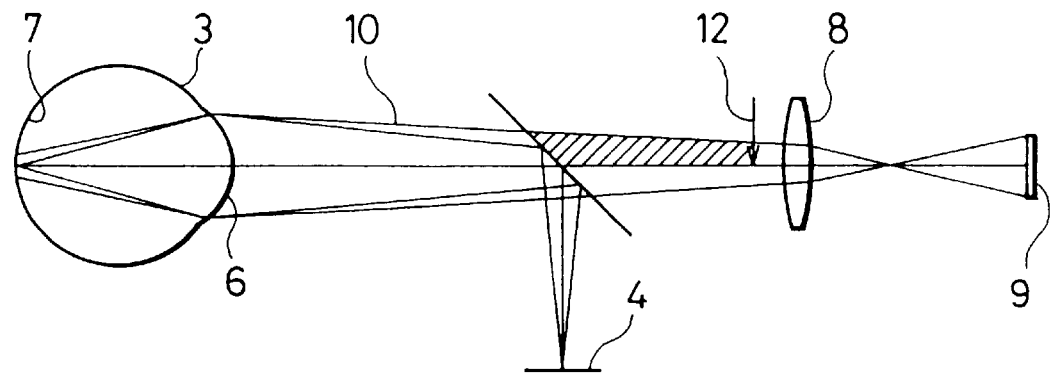

As shown in FIG. 3(C), in case diopter value of the eye under measurement 3 is positive compared with the standard diopter value, the image of the light source 4 is projected so that an image is formed behind the fundus 7. The reflection light beam 10 reflected by the fundus 7 is converged at a point behind the light blocking member 12, i.e. at a point closer to the photodetection element 9. In the reflection light beam 10 projected to the photodetection element 9, a portion of the light beam on opposite side to the light beam in FIG. 3(A) (upper half portion in the figure) is blocked.

In the light beam projected to the photodetection surface 9a, light amount distribution is changed according to whether the diopter value of the eye under measurement 3 is greater or smaller or positive or negative compared with the standard diopter value, and the diopter value can be determined according to the light amount distribution status.

The photodetection element 9 is used to detect light amount distribution of the light beam formed on the photodetection surface 9a. The arithmetic unit 13 detects light amount distribution of the light beam formed on the photodetection surface 9a based on the signal from the photodetection element 9 and judges whether ocular refractive power of the eye under measurement 3 is positive or negative compared with the standard diopter value and also calculates its absolute value. The results of the calculation are outputted to the display unit 14. The display unit 14 displays the obtained results.

In the above embodiment, a half-mirror is used as means for separating light beams, while it is needless to say that various types of light beam separating means such as a beam splitter, a polarizing prism, etc. may be used.

Referring to FIGS. 4(A)–(E), description will be given now on light amount distribution status of the light beam formed on the photodetection surface 9a.

To facilitate the explanation, in FIGS. 4(A)–(E), an optical axis of the light source 4 is aligned with the optical axis of the photodetection optical system, and the light blocking member 12 is made identical with the image-forming lens 8.

For this reason, the light source 4 and the image-forming lens 8 are shown at the same position, and light blocking member 12 is not shown in the figure.

In each of FIGS. 4(A)–(E), a case is shown where ocular refractive power D of the eye under measurement is negative with respect to the standard ocular refractive power D0. In the following description, it is assumed that the reflection light beam from the fundus 7 is all projected to the photodetection surface 9a through the image-forming lens 8. If it is supposed that the distance between the light source 4 and the pupil 6 of the eye under measurement is l, and that ocular refractive power of the eye under measurement is the standard ocular refractive power D0 when the image of the light source is focused on the fundus 7, it is given by the following equation (1):

$$D0 = -1000/l \quad (1)$$

Figure 4A:
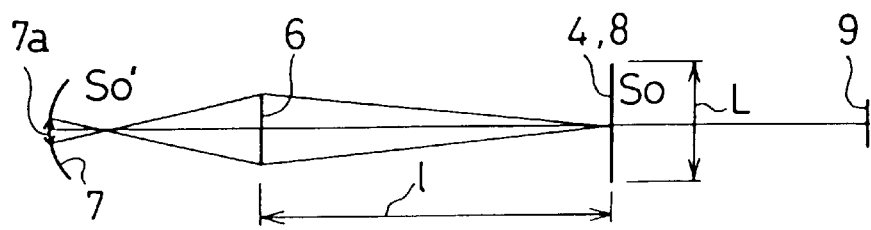
FIG. 4(A), FIG. 4(B), FIG. 4(C), FIG. 4(D) and FIG. 4(E) each represents a drawing to show photodetection and conditions of light beam reflected from fundus of the eye under measurement.

FIG. 4(A) shows that a projection light beam from a point S0 on the axis of the slit-like light source 4 having a length L is projected in a direction perpendicular to the optical axis when ocular refractive power of the eye under measurement is D (<D0). The image of the point S0 is formed at S0' for once, and it is projected as a blurred image on the fundus 7 of the eye under measurement. With the increase of the value of the difference (D0−D), an area 7a where the image is projected is widened.

Figure 4B:
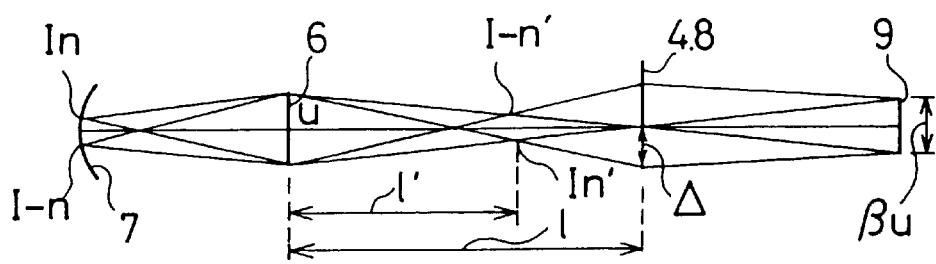

FIG. 4(B) shows a status of the photodetection optical system 2 and reflection light beam from the fundus 7 of the eye under measurement.

As shown in FIG. 4(B), when we consider the light beam from a point I-n at an end of a projection area on the fundus 7 of the eye under measurement, an image I-n' of this point is formed at a position with a distance of l' from the pupil 6 of the eye under measurement, and this light beam is projected to the photodetection element 9, which is placed at a position conjugate to the pupil 6 of the eye under measurement via the image-forming lens 8. Relational expression of this value of l' and ocular refractive power D of the eye under measurement is as follows:

$$D = -1000/l' \quad (2)$$

On the other hand, a spread width Δ on an edge of the light beam emitted from a point on the fundus 7 can be given by the following equation (3) as it is evident from FIG. 4(B) if it is supposed that pupil diameter of the eye under measurement is u:

$$\Delta = u \times (l - l')/l' \quad (3)$$

From the equations (1) and (2), the following equation (4) is obtained:

$$\begin{aligned}\Delta &= u \times (l = l')/l' \\ &= u\{(-1000/D0) - (-1000/D)\}/(-1000/D) \\ &= u(D/D0 - 1) \\ &= u \times (\Delta D/D0)\end{aligned} \quad (4)$$

where ΔD=D−D0

With the increase of the difference between the ocular refractive power D of the eye under measurement 3 and the standard ocular refractive power D0, spreading of the light blocking member 12 is increased.

Next, description will be given on spreading of light beam over the photodetection element 9. Regardless of ocular refractive power of the eye under measurement 3, the photodetection element 9 is arranged at position conjugate to the pupil 6 of the eye under measurement with respect to the image-forming lens 8. If it is supposed that diameter of the pupil 6 is u and multiplying factor of the image-forming lens 8 is β, a light beam is projected over a region with diameter of βu on the photodetection element 9.

The light beam coming from the point In, which is at a position symmetrical to the point I-n with respect to the optical axis, also forms an image In at the position with a distance of l' from the pupil 6, and the light beam is projected over the same region of βu on the photodetection element 9. If it is supposed that the light source 4 is a point light source and that there is no light blocking member 12, the light amount distribution on the photodetection element 9 is determined by integration of the light beam from points I-n, . . . I0, . . . In from the fundus 7.

Here, in order to discuss light amount distribution on the photodetection element 9, let us consider light beam, which enter at a position P-n of an end of light beam projecting position on the photodetection element 9, i.e. at coordinate position of −βu/2 having the optical axis as the center. Then, the light beam entering at this position is limited to the light beam within the range of the shaded portion A in FIG. 4(C). Similarly, if we consider light beam entering at a position Pn, which is symmetrical to the above position P-n with respect to the optical axis, the light beam is limited to the light beam within the range of the shaded portion A'. If an edge-like light blocking member 12 for cutting the light beam A' on one side of the optical axis is placed at a position with a distance 1 from the pupil 6 of the eye under measurement (conjugate position to the light source 4), the light beam entering the position P-n on the photodetection element 9 is not blocked by the light blocking member 12. The higher the position is moved up from the position of P-n, the more the light beam is blocked gradually. At the central position P0, half of the light beam is blocked. At the position of Pn, all beam is blocked. Therefore, because of the edge-like light blocking member 12, light amount distribution shows a certain fixed inclination, i.e. the higher the position on the photodetection element 9 is, the darker it becomes, and light amount is turned to 0 at the point Pn.

Figure 4C:
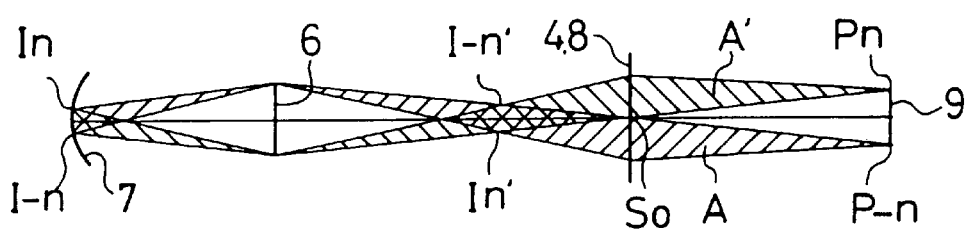
Figure 4D:
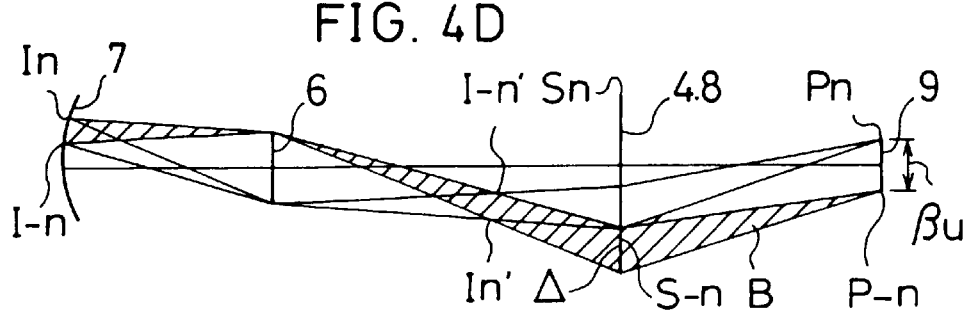

In FIGS. 4(A)–(C) as described above, only the light beam emitted from one point on the optical axis of the light source 4 has been described. However, if we consider the light beam coming from a point S-n at the end of the light source 4 (a point with coordinate position of −L/2 when the size of the light source is supposed to be L), it is as shown in FIG. 4(D). The light beam from the point S-n is projected to a region from the point I-n to the point In on the fundus 7 as shown in FIG. 4 (D). The reflection light beam from the point I-n and the point In form the images of I-n' and In' at a position with a distance of l' from the pupil 6 of the eye under measurement as described above, and the light beam is then projected to an area with diameter of βu on the photodetection element 9. Here, among the light beam emitted from the point S-n at the end of the light source 4, the light beam entering the point P-n at the end of the light beam projected on the photodetection element 9 are the light beam in the shaded portion B in FIG. 4(D).

Figure 4E:
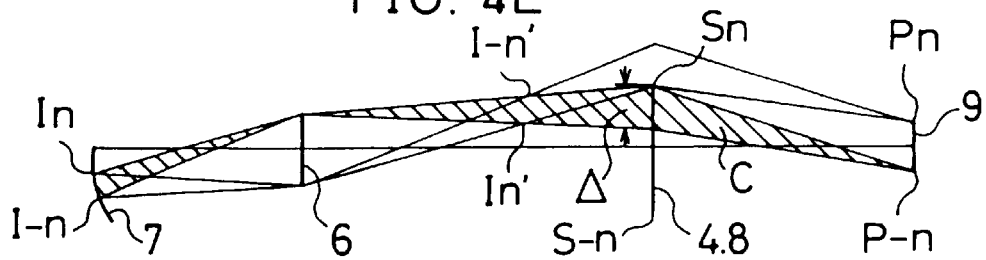

If we consider the light beam coming from a point Sn of the light source 4, which is at symmetrical position to the point S-n as described above, and if we also consider the light beam entering the point P-n on the photodetection element 9, the light beam is the beam entering the shaded portion C in FIG. 4(E). In this way, if it is supposed that the light source 4 has a certain size, the light amount on a point on the photodetection element 9 must be considered as a total sum of the light beam coming from each of the points of the light source 4.

Figure 5A:
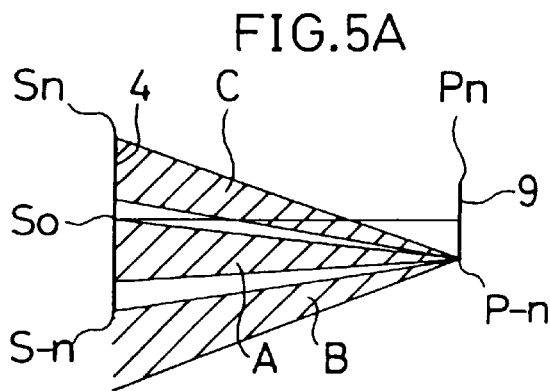
FIG. 5(A) shows a status of reflected light beam from points on a light source reaching a photodetection element.

FIG. 5(A) shows the light beam entering the position P-n on the photodetection element 9 as overlapped light beam based on the above concept. Among the light beam emitted from the position S-n of the light source 4, the light beam entering the position P-n is projected in an area B (See FIG. 4(D)). The higher the position is moved up on the light source 4, the light beam is also moved upward. At the position S0 of the light source on the axis, it is the light beam projected in an area A (See FIG. 4(C)). At the position Sn on the light source 4, it is the light beam projected in an area C (See FIG. 4(E)). Therefore, light amount at the point P-n on the photodetection element 9 is considered to be the total sum of these light beam.

Figure 5B:
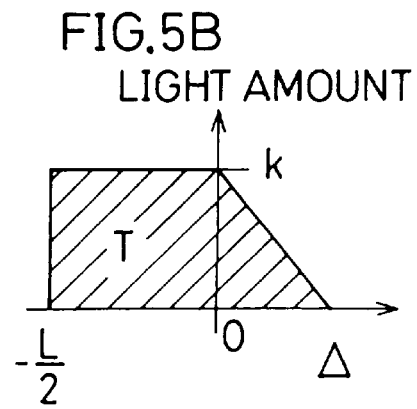
FIG. 5(B) shows changes of light amount of each light beam when the light beam is blocked by a light blocking member.

FIG. 5(B) is a diagram showing light amount at the point P-n on the photodetection element 9 when the light blocking member 12 is placed at a position with a distance of l from the pupil 6 of the eye under measurement.

FIG. 5(B) shows how the light beam is blocked by the light blocking member 12 as the position on the light source 4 is changed. The axis of abscissa in FIG. 5(B) indicates coordinate position on the light source 4, and the axis of ordinate denotes light amount. When we consider light beam coming from each of the points on the light source 4, the light beam from a point with coordinate position of −L/2 (L indicates the size of the light source) to the point 0 is not blocked by the light blocking member 12. When the light beam passes through the point 0, light is gradually blocked. At the point with coordinate position of Δ (the light beam is spread as described above), all of the light beam is blocked.

In FIG. 5(B), the light amount from each of the points on the light source is supposed to be k when the light beam is not blocked, and contribution of the light amount from each of the points on the light source is shown. The area of the shaded portion corresponds to a value of light amount at a point P-n on the photodetection element. The value T of the area can be given by the following equation (5):

$$T = \tfrac{1}{2} k (L+\Delta) \tag{5}$$

Figure 6A:
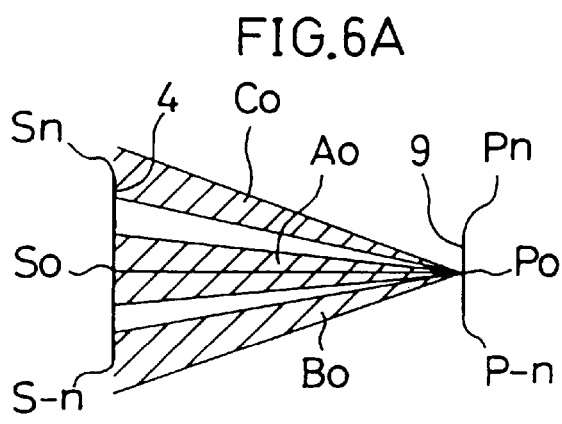
FIG. 6(A) shows a status of reflected light beam from points on a light source reaching a photodetection element.
Figure 6B:
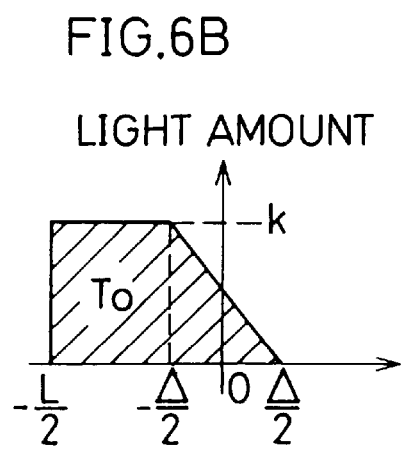
FIG. 6(B) shows changes of light amount of each light beam when the light beam is blocked by a light blocking member.

Similarly, let us consider the other points on the photodetection element 9. FIG. 6(A) shows the light beam entering the central point P0 on the photodetection element 9 in the same manner as in FIG. 5(A). Among the light beam coming from a point S-n on the light source 4, the light beam entering a point P0 is the beam within a shaded region B0, the light beam from the central point S0 on the light source 4 is the beam within a shaded region A0, and the light beam from a point Sn on the light source 4 is the beam within a shaded region C0. Light amount entering the center P0 of the photodetection element 9 corresponds to the area T0 of the shaded region in FIG. 6(B). That is, when we consider the light beam entering the central point P0 of the photodetection element 9 from each of the points on the light source 4, light beam is not blocked from a point with coordinate of −L/2 on the light source 4 to a position of −Δ/2. When the light beam passes through the position of −Δ/2, the light beam is gradually blocked, and all light beam is blocked at the position of Δ/2. The area value T0 can be calculated as given by the following equation (6):

$$T0 = k L/2 \tag{6}$$

Figure 7A:
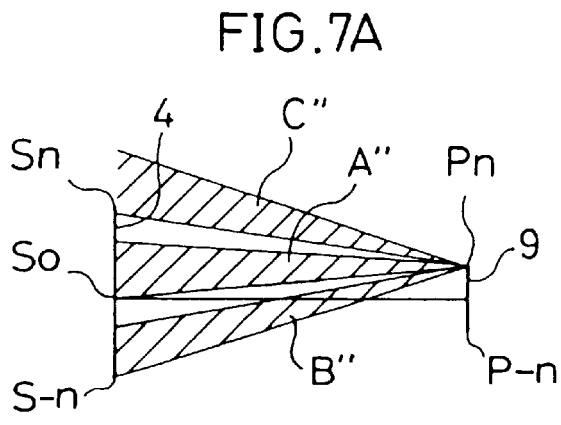
FIG. 7(A) shows a status of reflected light beam from each of the points on a light source reaching the photodetection element.
Figure 7B:
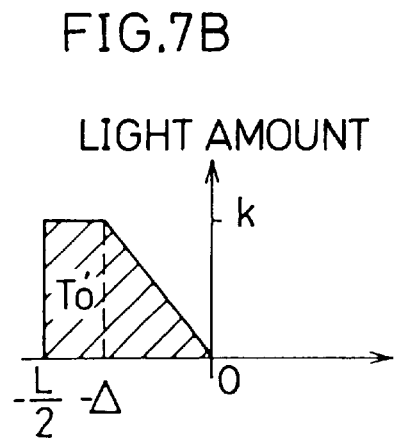
FIG. 7(B) shows changes of light amount of each light beam when the light beam is blocked by a light blocking member.

Similarly, a status of the light beam entering a point Pn on the photodetection element 9 and light amount value on this point are shown in FIG. 7(A) and FIG. 7(B). In FIG. 7(A), among the light beam coming from a point S-n on the light source 4, the light beam entering a point Pn are those within a shaded region B", light beam from a point S0 at the center of the light source 4 is that within a shaded region A", and light beam from a point Sn on the light source 4 is that within a shaded region C". In this case, as shown in FIG. 7(B), when we consider the light beam entering a point Pn on the photodetection element from each of the points on the light source 4, light beam is not blocked from a position of −L/2 on the light source to a position of −Δ. When the light beam passes through the position of −Δ, light beam is gradually blocked, and all light beam is blocked at a position of 0. The area value T0' can be calculated as given by the equation (7):

$$T0' = k (L-\Delta)/2 \tag{7}$$

As it is evident from the results of the equations (5), (6) and (7), the higher the position on the photodetection element 9 is, the more the light amount value is gradually decreased. When light amount distribution on the photodetection element 9 is shown in the figure, it is given as linear change as shown in FIG. 8.

In the above, description has been given under the assumption that the spread width Δ on the light blocking member 12 is smaller than ½ of the size L of the light source when we consider a light beam emitted from a point on eye fundus.

Next, when ocular refractive power of the eye under measurement 3 as shown in FIG. 3(B) is at the standard value, it is possible to determine light amount distribution on the photodetection element 9 as described above even in case where ocular refractive power of the eye under measurement 3 is positive compared with the standard value as shown in FIG. 3(C). In this case, if ocular refractive power of the eye under measurement 3 is at the standard value, it is uniform distribution as shown in FIG. 9. If ocular refractive power of the eye under measurement 3 is positive, it is as shown in FIG. 10, which is a distribution opposite to the one shown in FIG. 8.

The inclination of the light amount distribution as described above shows diopter value (ocular refractive power), and the direction of inclination indicates whether the diopter value is positive or negative. In the following, description will be given in connection with FIG. 11.

If it is defined that inclination of the light amount distribution is Δf/f0, then:

$$\Delta f/f0 = (k\Delta/2)/(kL/2) = \Delta/L \tag{8}$$

Spreading Δ of the light beam, i.e. blur amount Δ, can be calculated from the equation (4) as given by the following equation (9):

$$\Delta = u \times (l-l')/l' = u \times \Delta D/D0 \tag{9}$$

Therefore, from the equation (8), the following equation (10) can be obtained:

$$\Delta f/f0 = u\Delta D/LD0$$

$$\therefore D = (LD0/u)(\Delta f/f0)$$

$$\Delta D = K(\Delta f/f0), \quad (K = LD0/u) \tag{10}$$

The equation (10) indicates that deviation ΔD of diopter value of the eye under measurement with respect to the standard diopter value D0 is proportional to Δf/f0. Accordingly, the deviation Δ of diopter value of the eye under measurement can be obtained by determining the value of Δf/f0 from light amount distribution. Further, the diopter value D can be obtained from the following equation (11):

$$D = D0 + \Delta D \tag{11}$$

As described above, the diopter value of the eye under measurement can be determined from light amount distribution of the light beam is reflected from the fundus. The light amount distribution as given above is merely a schematical representation. In reality, there are changes in light amount corresponding to each part of eye ball as shown in FIG. 12(A) (See FIG. 12(B); Light amount distribution shown in FIG. 12(B) indicates light amount distribution at the standard diopter value.), i.e. the changes such as protrusion ρ of light amount at a luminescent spot 21 due to reflection of cornea, or dropping σ of light amount at iris 20, which is at a position deviated from the pupil 6. Further, there are various factors such as blinking at measurement, or eyelashes, turbidity of lens, etc., which exert influence on the results of measurement.

In this respect, more concrete explanation will be given below.

Figure 14:
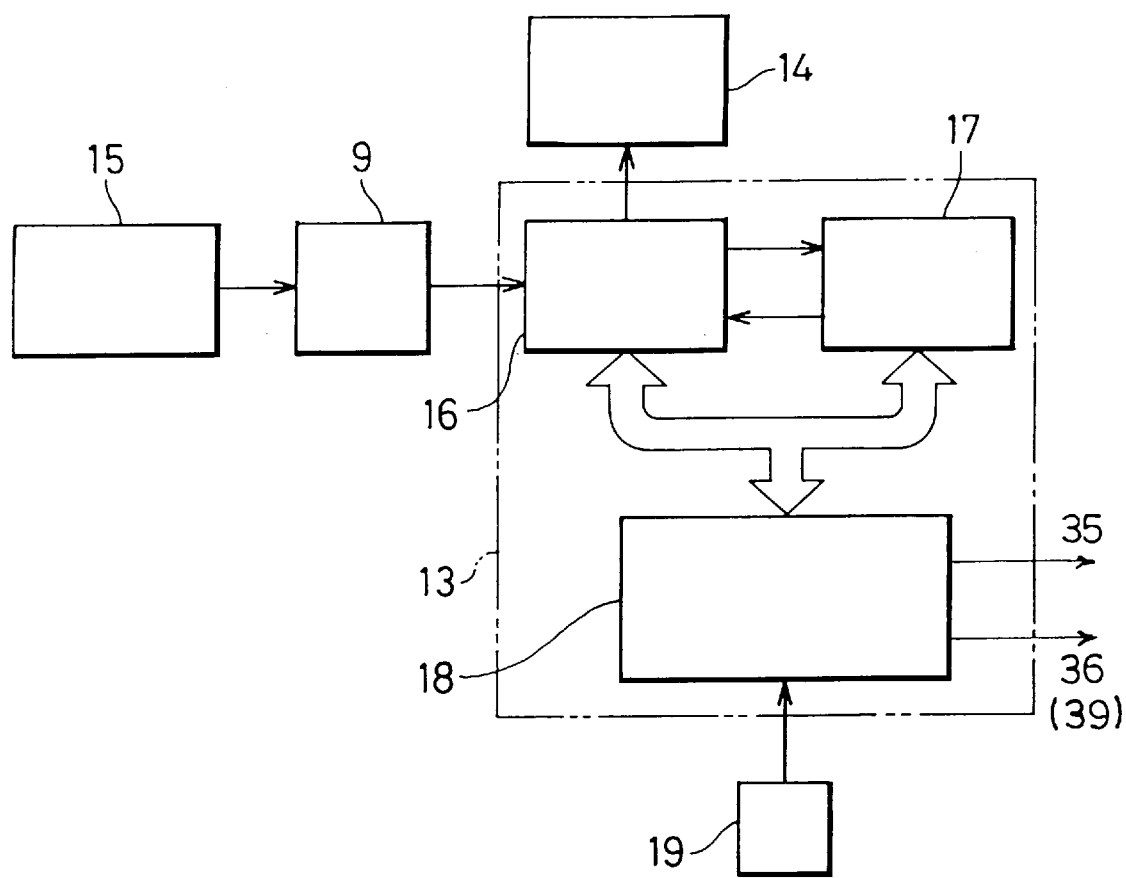
FIG. 14 is a block diagram to show a condition in the above embodiment.

In FIG. 14, reference numeral 15 represents a measuring optical system of an ophthalmologic measuring system as described above, 9 indicates a photodetection element, 13 an arithmetic unit, 14 a display unit, 16 a frame memory to store an image on the photodetection element 9 and results of arithmetic processing unit, 17 an arithmetic processing unit, 18 indicates a control unit, which gives sequence commands such as synchronizing command for the frame memory 16 and the arithmetic processing unit 17, switching of on-off of the first gaze target 35 and the second gaze target 36, incorporation of data from the photodetection element 9, etc., and 19 is a switch for starting measurement.

In the following, referring to FIG. 15–FIG. 24, description will be given on measurement operation on the eye under measurement 3 under the condition, for example, when the first gaze target 35 in FIG. 1 is turned on and a person under measurement is asked to collimate the first target 35.

Figure 16A:
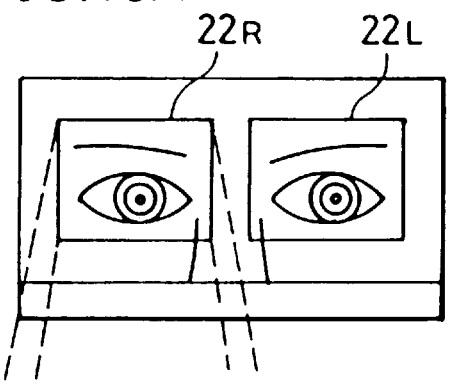
FIG. 16(A) is a drawing to show an image-taking screen of the ophthalmologic measuring system.

First, the examiner observes an image of the eye under measurement as displayed on the display unit 14. FIG. 16(A) shows a screen on the display unit 14. On the display unit 14, images of the eyes under measurement are displayed by overlapping on standard targets 22R and 22L indicating a certain fixed area. At the center of the pupil of each of the images of the eyes to be measured, a luminescent spot image formed by a light beam reflected from cornea of the eye under measurement is formed among the light beam coming from the light source 4. The examiner confirms that both eye images are within the standard targets 22R and 22L and approximate alignment and adjustment have been completed and that the person under measurement is collimating in straight direction. Then, the measurement starting switch 19 is turned on. When this switch 19 is turned on, an image signal from the photodetection element 9 is incorporated in the frame memory 16 and is stored. By single operation of the measurement starting switch 19, a plurality of image signals are automatically and continuously stored at a predetermined time interval in the frame memory 16 in association with the incorporation time.

The time interval to incorporate a plurality of image signals is set in such manner that changes of factors such as ocular refractive power, pupil diameter and interpupillary distance of the eye under measurement can be detected. If it is supposed that the time interval is 1/15 second, 15 frames can be incorporated within a second. It is desirable to set the incorporation time interval in such manner that several frames or more can be incorporated within a second.

Based on the image stored in the frame memory 16, the arithmetic processing unit 17 performs arithmetic processing according to the steps given below. In the calculation of the arithmetic processing unit 17, after the stored image has been incorporated, measurement is performed on the right eye. Then, measurement is performed on the left eye. In the following, description will be given referring to FIG. 15.

First, a position of a luminescent spot image formed by corneal reflex is detected (S3).

Figure 16B:
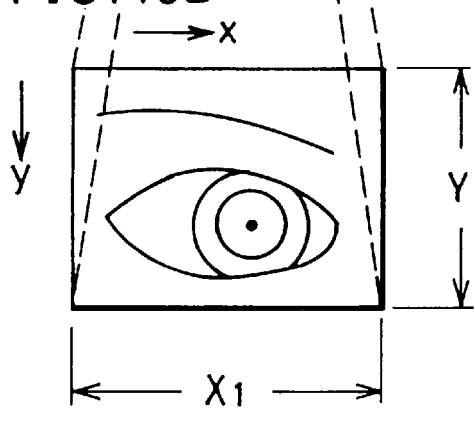
FIG. 16(B) is an enlarged view of an eye under measurement.

The image stored in the frame memory 16 is taken in such manner that both eyes are included within a predetermined area (which corresponds to the area of the standard targets 22R and 22L as described above), e.g. the right eye is included in an area (X1; Y1). FIG. 16(B) gives an enlarged view of this area.

Figure 16C:
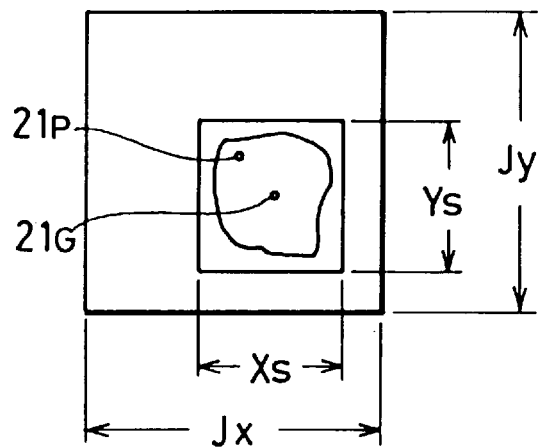
FIG. 16(C) is a drawing to show an image of a luminescent spot.

Within the area (X1; Y1) of the frame memory 16, light amount is compared in picture elements of the photodetection element 9, and a point 21p is obtained, which has the highest light amount value. The point 21p is a point having the highest light amount among the luminescent spot images. FIG. 16(C) is an enlarged view of a region surrounding this luminescent spot. Next, a certain fixed area (Jx; Jy) is set with the brightest point 21p at the center. Within this area, light amount values of images are compared and points having images higher than a predetermined level are extracted. Then, a position 21G of weighted center of a graphical shape of the luminescent spot image formed by these points is calculated (hereinafter referred as luminescent spot weighted center or weighted point).

Next, a certain fixed area (to be described later) (Xs; Ys) for eliminating the luminescent spot is set with the luminescent spot 21G at the center. The center of the luminescent spot formed by corneal reflex is not necessarily the brightest spot, and if a fixed area for eliminating the luminescent spot is determined with the brightest point 21p at the center, the luminescent spot image may be out of this area. However, if the luminescent spot weighted point 21G is set at the center as described above, there is no such possibility.

The luminescent spot weighted point has been determined for the right eye. Then, based on the position of the luminescent spot weighted point, elimination of the luminescent spot in the right eye is performed (S3).

Figure 18A:
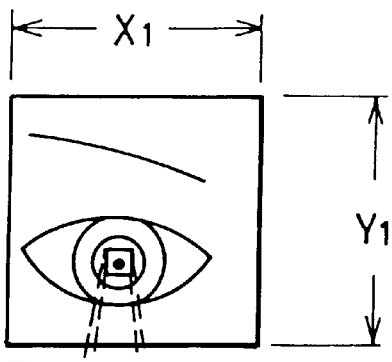
FIG. 18(A) is an enlarged view of an eye under measurement similar to the drawing of FIG. 16(B)
Figure 18B:
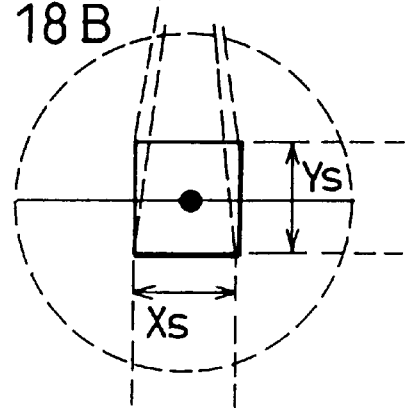
FIG. 18(B) is a drawing to show a range of an area including a luminescent spot.
Figure 18D:
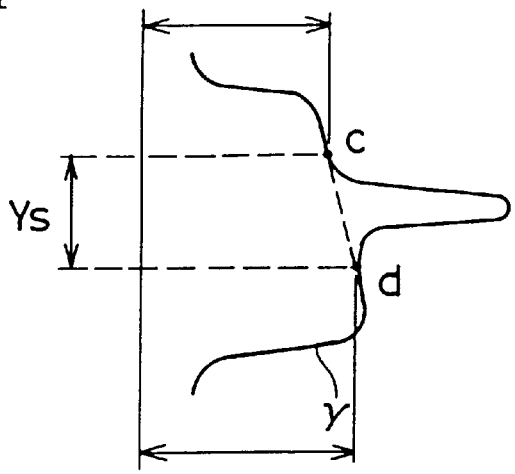
FIG. 18(D) is a diagram to show light amount distribution on a scanning line running perpendicularly to the edge.

When the luminescent spot weighted point has been obtained, a detection area (Xs; Ys) near the luminescent spot with the luminescent spot weighted point at the center is set as shown in FIG. 18(B). Light amount at a point "a" and a point "b" are obtained where the scanning line in X direction in parallel to the edge crosses boundary lines of the detection area (Xs; Ys), and these points "a" and "b" are approximated by straight line. The straight line connecting the point "a" with the point "b" indicates light amount distribution where influence of the luminescent spot on the scanning line in X direction in the detection area (Xs; Ys) has been eliminated. (See FIG. 18(C); In the figure, light amount distribution shown by the symbol δ shows light amount distribution curve, which is obtained by scanning of the pupil in X direction.)

The equation of approximate straight line between the points "a" and "b" is given as the equation (12).

$$L = \{(Lb - La)/Xs\} \times X + La \tag{12}$$

The scanning as described above is performed over the total range of the detection area (Xs; Ys), and correction values by eliminating the influence of luminescent spot is determined for the detection area (Xs; Ys), and these values are stored.

Next, light amount is obtained at a point "c" and a point "d" where the scanning line crosses the boundary line of the detection area (Xs; Ys) using the scanning line in Y direction, which is perpendicular to the edge, and these points "c" and "d" are approximated by straight line.

The approximated straight line is given by the equation (12'):

$$L' = \{(Ld-Lc)/Ys\} \times Y + Lc \qquad (12')$$

The scanning as described above is performed over the total range of the detection area (Xs; Ys), and correction values by eliminating influence of luminescent spot are obtained for the scanning in Y direction, and these values are stored.

Further, X direction scanning correction value and Y direction scanning correction value are compared one after another in the light amount value of picture element for the same coordinates. The light amount, which is higher in the result of the comparison, is stored as the final value at the coordinates. What has been obtained by this comparison is an image signal of the detection area (Xs; Ys) with the luminescent spot eliminated. The stored value for the detection area (Xs; Ys) of the frame memory 16 is replaced by the correction value obtained from the comparison, and what is replaced by the correction value is newly stored in the frame memory 16 as a corrected image. The corrected image with luminescent spot thus eliminated is displayed on the display unit 14 together with the image before correction (See FIG. 19).

Here, the higher light amount is selected in the comparison of X direction scanning correction value with Y direction scanning correction value. This is because, in the measurement, there are factors such as eyelashes, turbidity of lens, etc., which exert influence and decrease light amount as measurement errors. Therefore, if higher light amount is selected, a value closer to the true value can be obtained.

Next, the detection area is enlarged to an area (X2; Y2), which is a sufficiently wide region for including the eye with the weighted point of luminescent spot at the center (FIG. 20(B)). By scanning the detection area (X2; Y2) in X direction (a direction running in parallel to the edge) in the corrected image or by scanning in Y direction (a direction running perpendicularly to the edge), light amount distribution on the scanning line is obtained. From the light amount distribution thus obtained, pupil diameter u can be determined (S4).

Figure 18C:
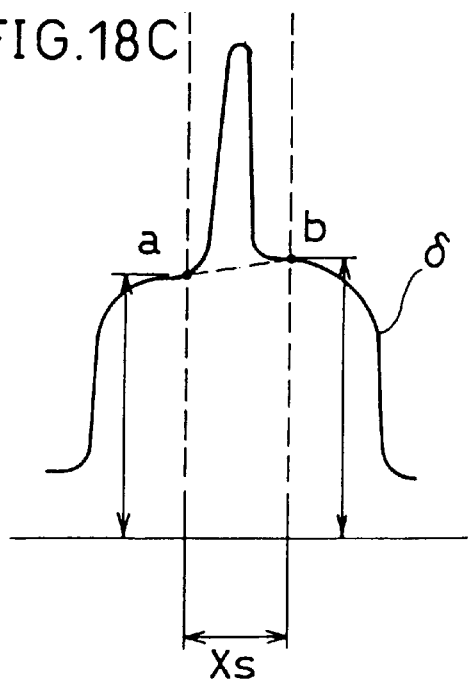
FIG. 18(C) is a diagram to show light amount distribution on a scanning line running in parallel to an edge passing through a luminescent spot.

As shown in FIGS. 12(A), (B) and (C), in the region of the iris 20, which is at a position deviated from the pupil 6, light amount is suddenly decreased (FIG. 18(C)). When change rate of the light amount distribution γ is obtained, the value is protruding at boundary points of m and n on the pupil 6 and the iris region 20. Coordinate positions of these boundary points m and n are read from the frame memory 16, and pupil diameter u can be determined by calculation of the arithmetic processing unit 17.

Next, when blinking occurs as shown in FIG. 13(A), eyelid partially covers the pupil 6, and light amount decreases on upper portion of the pupil 6 which is partially covered. For this reason, in the light amount distribution, it looks as if boundary position m' of the eyelid is the boundary position of the pupil 6. In this respect, if the pupil diameter u is calculated under the condition shown in FIG. 13(A), the calculated value is smaller than the actual value.

FIG. 12(B) and FIG. 13(B) each represents light amount distribution seen on the scanning line in vertical direction. Similar light amount distribution can be obtained by the scanning line in horizontal direction. Therefore, the pupil diameter u obtained from the light amount distribution in horizontal direction is a value not influenced by blinking. A pupil diameter uV in vertical direction and a pupil diameter uH in horizontal direction are obtained by the arithmetic processing unit 17. Further, ratio of the pupil diameter uV in vertical direction to the pupil diameter uH in horizontal direction, i.e. uV/uH, is obtained. If this ratio is smaller than a predetermined value (ideally, it is 1), it is judged that there has been blinking.

Blinking can also be detected by utilizing the luminescent spot weighted point 21G. Because this luminescent spot weighted point 21G is at the center of the pupil 6, blinking can be detected by monitoring a distance between the luminescent spot weighted point ρ and boundary positions m or n of the pupil 6.

Line segments ρm and ρn are calculated by the arithmetic processing unit 17, and ratio of these two line segments is obtained and this ratio is monitored.

Specifically, in case there is no blinking, the ratio a line segment ρm/a line segment ρn=1. If there is blinking, the ratio a line segment ρm'/a line segment ρn<1. Blinking can also be detected as follows: Integration is performed up to the boundary points m, m' and n in the light amount distribution curve, and the integration value is compared in the same manner as described above.

In the present system, ocular refractive power is obtained from the inclination of light amount distribution. If it is judged that there has been blinking, it is not advanced to the next step. On the other image signals incorporated in the frame memory 16, the processing as described above is repeatedly performed. Then, if it is judged that there has been no blinking, ocular refractive power is calculated as described below.

On the corrected image as described above, scanning is performed on the detection area (X2; Y2) in Y direction (a direction perpendicular to the edge), and light amount distribution on the scanned line is obtained. There are a plurality of scanning lines to obtain light amount distribution, i.e. scanning line passing through the luminescent spot weighted point and scanning lines deviated to −X side and +X side (FIG. 21(A)).

Figure 19:
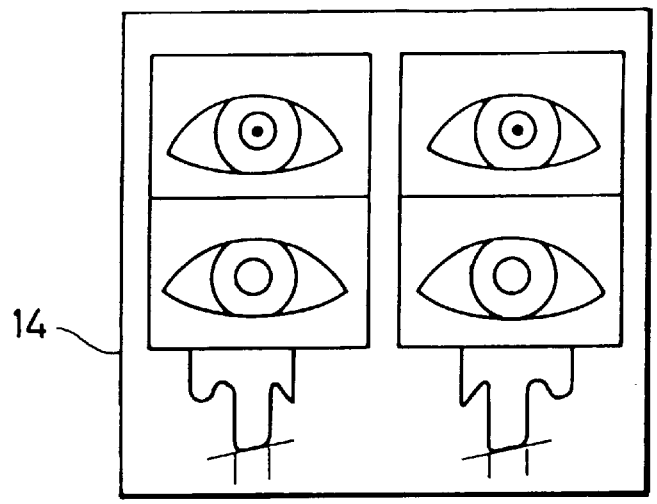
FIG. 19 is a drawing of a display screen of a display unit.
Figure 20A:
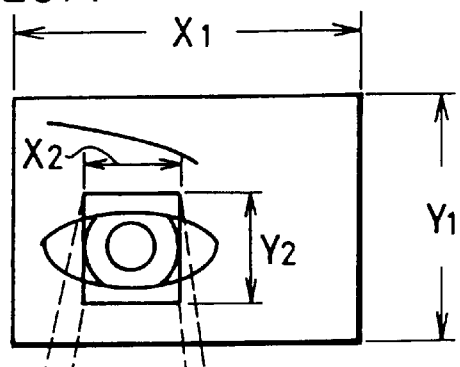
FIG. 20(A) is an enlarged view of an eye under measurement similar to that of FIG. 16(B)
Figure 20B:
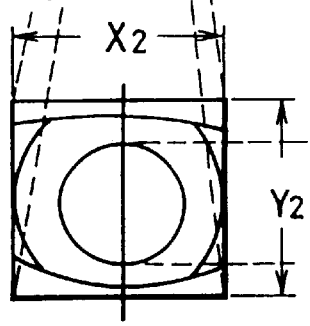
FIG. 20(B) is a drawing to show a scanning region including a pupil.
Figure 20C:
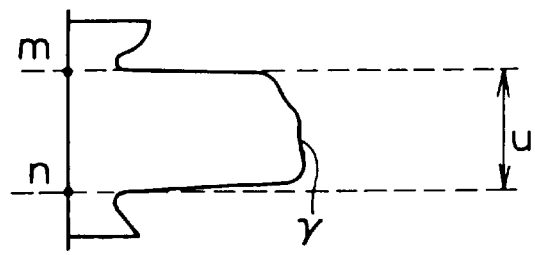
FIG. 20(C) is a diagram to show light amount distribution on a scanning line running perpendicularly to the edge.
Figures 21A, 21B, 21C:
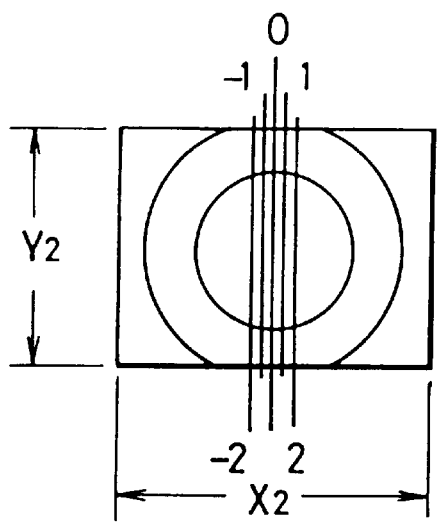
FIG. 21(A), FIG. 21(B), and FIG. 21(C) each represents a drawing, through which averaged light amount distribution can be obtained.
Figure 22:
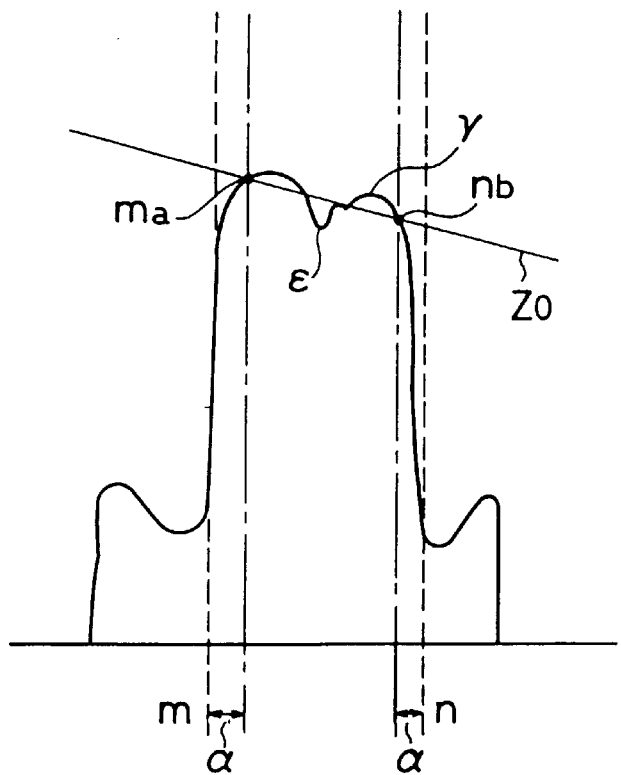
FIG. 22 is a diagram to show relationship between light amount distribution and an approximated straight line.

On the light amount distribution thus obtained, average light amount of each picture element of the same coordinates in Y direction of each scanning line is calculated. The average value is substituted as light amount value of the scanning line passing through the luminescent spot weighted point and is stored (FIGS. 21(B) and (C)). FIG. 22 shows light amount distribution obtained by this substitution. The averaged light amount distribution is displayed on the display unit 14 together with the images of both eyes (FIG. 19).

By the display of the averaged light amount distribution, the examiner can judge ocular refractive power of the person under measurement by visual inspection. Averaging is performed from the light amount distribution shown in FIG. 19, and it is corrected to light amount distribution for linear measurement as shown in FIG. 11. As shown in the figure, the curve is drooped near the boundary of the pupil, and this is because light scatters on iris edge. In order to correct this, the component a near the boundary of the pupil should be eliminated, and light amount distribution for linear measurement is obtained. To obtain the light amount distribution for measurement, the least square approximation method is used, for example.

The straight line obtained by this approximation method is shown by Z0 in FIG. 22. Using this straight line Z0, the ratio Δf/f0 required for calculation of diopter value can be obtained. In the averaged light amount distribution, however, there is dropping caused by factors such as influence of eyelashes, turbidity of lens, etc. as shown by the symbol ϵ. Therefore, in order to obtain the light amount distribution with higher accuracy, it is necessary to minimize the influence of this drop ϵ.

Figure 23:
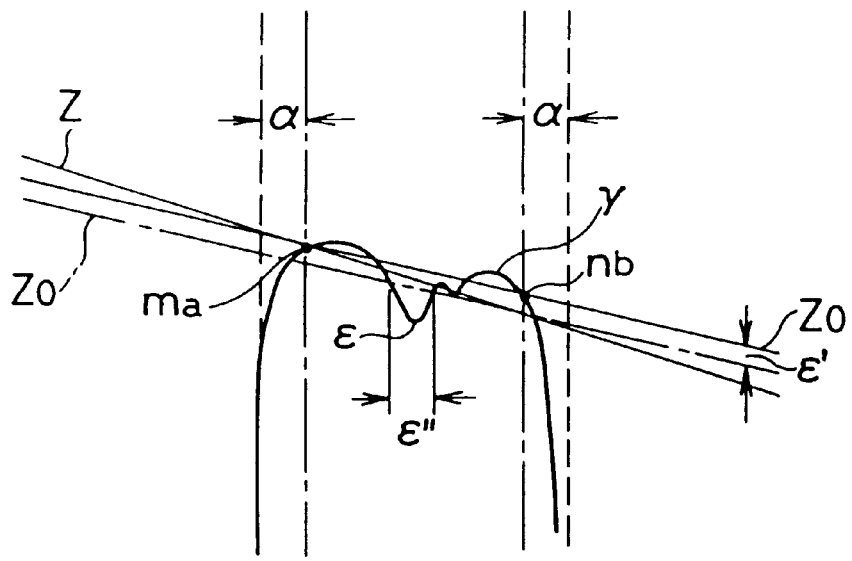
FIG. 23 is a drawing to show how to obtain the approximated straight line.

One of the methods for such purpose is as follows: As shown in FIG. 23, a straight line Z0' having a level by ϵ' lower than the straight line Z0 is used as a reference. The value having a level lower than the straight line Z0' (i.e. a value within the range shown by the symbol ϵ" in FIG. 23) is not used as the data in the approximation, and approximation is performed, and a straight line Z thus obtained is regarded as the light amount distribution for measurement.

Figure 24:
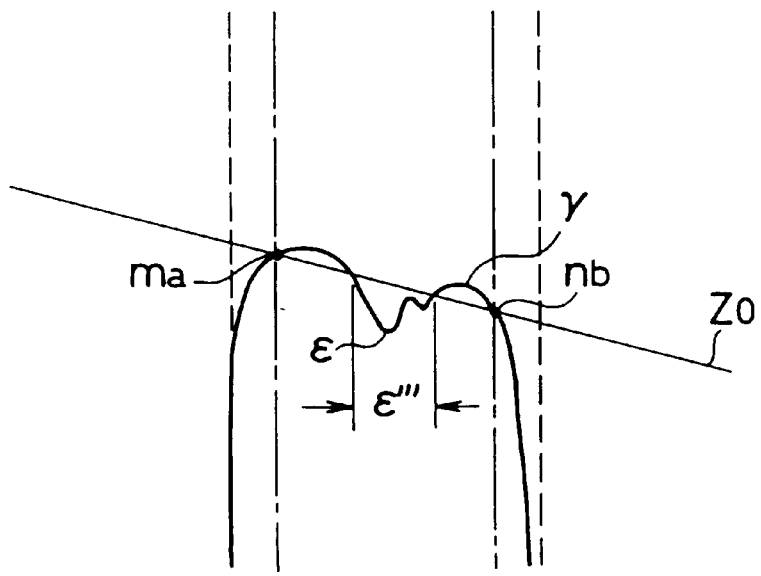
FIG. 24 is a drawing to show how to obtain the approximated straight line.

There is another method which is explained as follows: As shown in FIG. 24, the value is replaced with the value of the straight line Z0 for the range with a level lower than the straight line Z0 (the range shown by the symbol ϵ''' in FIG. 24), and the averaged light amount distribution is corrected. Using this corrected and averaged light amount distribution, approximation is performed by the least square method. This procedure is repeated further, and the light amount distribution for measurement is obtained.

By the light amount distribution for measurement, deviation Δ of the diopter value of the eye to be measured can be determined from the equation (9) and the ratio Δf/f0 can be obtained from the equation (8). Further, diopter value D can be obtained from the equation (11).

When measurement has been completed for the right eye, measurement for the left eye is performed in the same manner (S2'). When the measurement for the left eye has been completed, interpupillary distance PD is determined according to the result of measurement on both eyes (S8).

Figure 17:
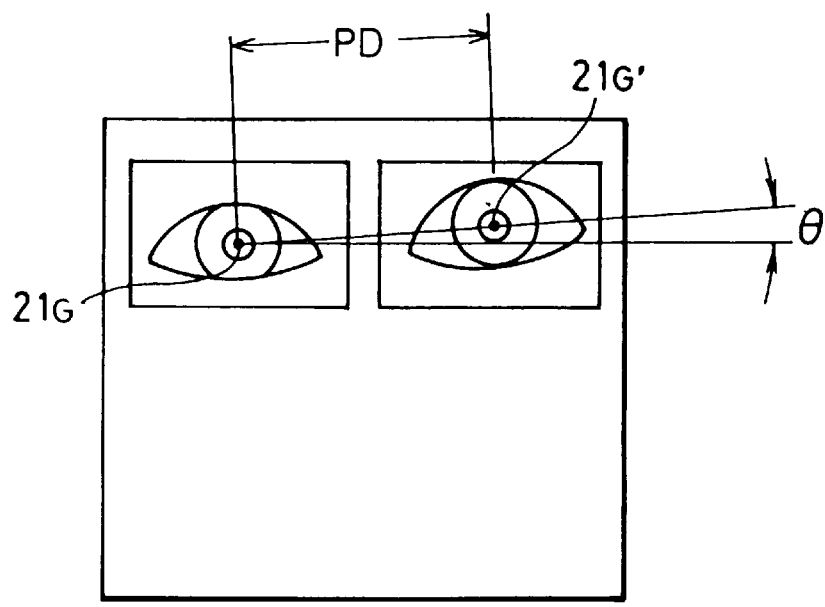
FIG. 17 is a drawing to show an image-taking screen in the ophthalmologic measuring system.

The interpupillary distance is calculated according to positions 21G and 21G' of the luminescent spot weighted point. That is, by obtaining the distance of the positions 21G and 21G' of the luminescent spot weighted points, the interpupillary distance PD can be determined. Further, inclination θ of the straight line connecting the luminescent spot weighted positions 21G and 21G' is obtained (FIG. 17). By obtaining the interpupillary distance PD between the two luminescent spots, the distance between the two eyes of the person under measurement can be determined, and by obtaining inclination θ of the straight line connecting the two luminescent spots, it is possible to detect at what angle the person under measurement is tilted with respect to the measuring system.

The data such as refractive power, pupil diameter and interpupillary distance for the two eyes are stored in the frame memory in association with the measuring time (S9), and image-taking for the measurement is completed.

In the above, description has been given on the measurement of ocular refractive power, pupil diameter and interpupillary distance in case gaze targets are specified. Next, description will be given on the measurement of changes over time of ocular refractive power, pupil diameter, and interpupillary distance relating to the eye to be measured when the distance of the gaze targets to be collimated by the person under measurement is changed.

In this measurement, when the measurement starting switch 19 is operated by the examiner, the control unit 18 turns the first gaze target 35 on and then switches over to the second gaze target 36, and target position to be instructed to the person under measurement is changed. Further, the control unit 18 incorporates an image signal from the photodetection element 9 before and after the change of target position by the switch operation. By the procedure as described above, data for each predetermined time interval for a first predetermined period and data for each predetermined time interval for a second predetermined period after the change of target position by switch operation are calculated, and the data are stored in the frame memory 16 in association with the measuring time.

Figure 25:
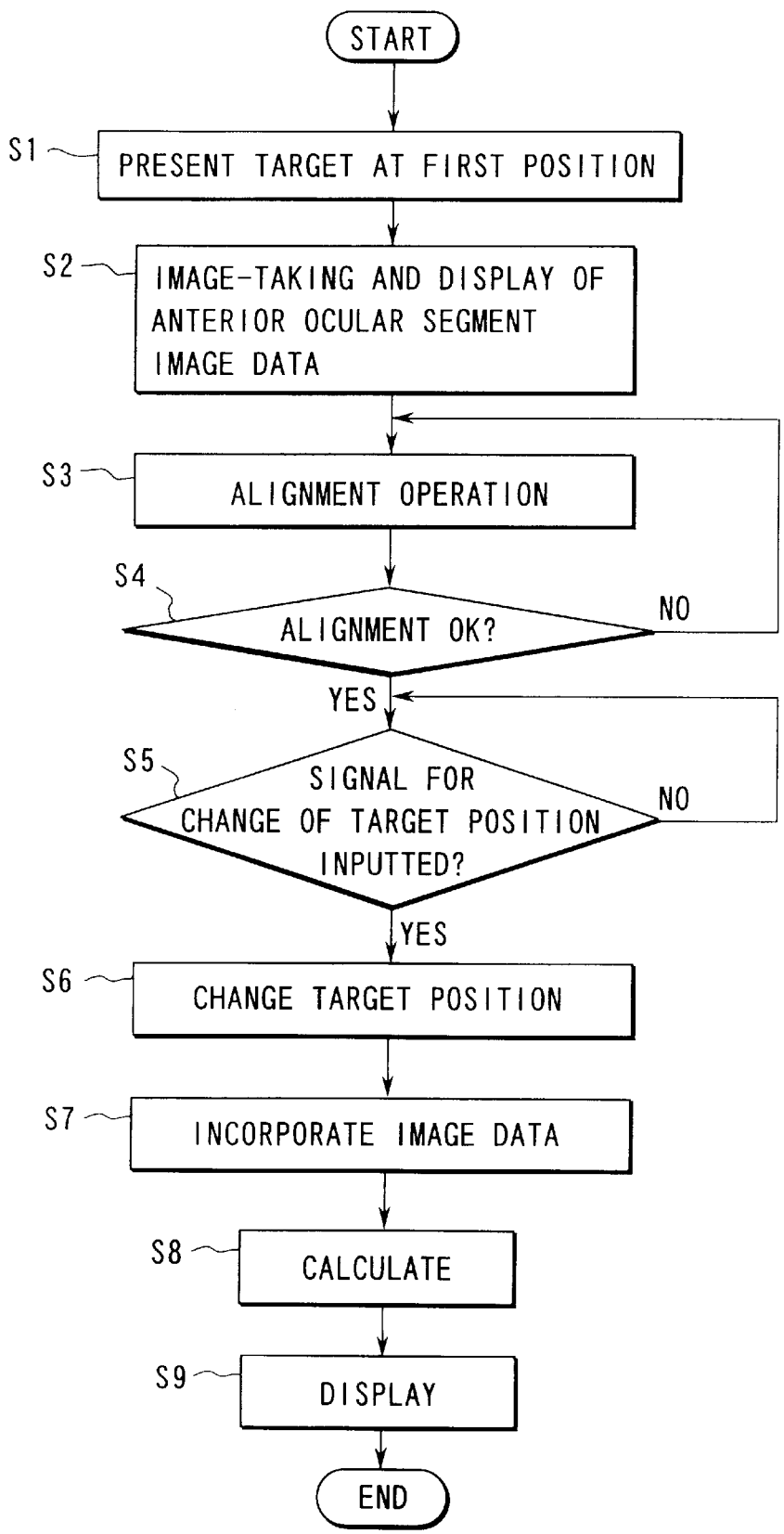
FIG. 25 is a flow chart showing a first measuring method.

Based on the above embodiment, description will be given now on the measurement of the changes over time of ocular refractive power, interpupillary distance and pupil diameter of the eye to be measured when it is switched over from the first gaze target 35 to the second gaze target 36 (i.e. from "far" to "near"), referring to FIG. 25.

S1: At the start of the measurement, the first gaze target 35 (a first position) is turned on, and the person under measurement collimates the target at far position (e.g. 2 m).

S2: A photodetection signal received at the photodetection element 9 is received by the arithmetic unit 13, and it is stored in the frame memory 16 as image data of anterior ocular segment including the two eyes of the person under measurement. The image data of the anterior ocular segment is displayed on the display unit 14 such as monitor unit.

S3: On the display unit 14, data such as scale for alignment are displayed at the same time, and the image of the displayed anterior ocular segment is aligned using the data such as scale as a reference (alignment).

S4: This alignment procedure is repeated until correct position is reached. When correct position is reached, it is ready to receive measurement starting signal from the measurement stating switch 19.

S5: The measurement starting signal is now in standby status, and this means the change of target position, and the measurement starting signal is inputted.

S6: The control unit 18 switches over the target from the first gaze target 35 (the first position) to the second gaze target 36 (the second position; e.g. 0.4 m).

S7: When the measurement starting signal is inputted, a photodetection signal corresponding to an image of anterior ocular segment from the photodetection element 9 is incorporated by the arithmetic unit 13 at a predetermined time interval during a predetermined period of time. The incorporated data are stored in the frame memory 16 in association with the measuring time.

S8: Based on the first target position data and the second target position data stored in the storage unit, ocular refractive power, pupil diameter and interpupillary distance (PD) of the two eyes before and after the change of target position are calculated. The measurement data are stored in association with the measuring time.

S9: The following calculation results are displayed:

Using light amount distribution of pupil images in the first target position data and the second target position data, ocular refractive power of each of the two eyes is calculated.

From the size of pupil images in the first target position data and the second target position data, pupil diameter of each of the left eye and the right eye is calculated.

Weighted position of each of left and right pupil images in the first target position data and the second target position data is determined, and interpupillary distance (PD) is calculated from the distance between the pupils.

Ocular refractive power, pupil diameter and interpupillary distance (PD) of each of the eyes before and after the change of target position as obtained by calculation are displayed on the display unit 14.

Figure 26:
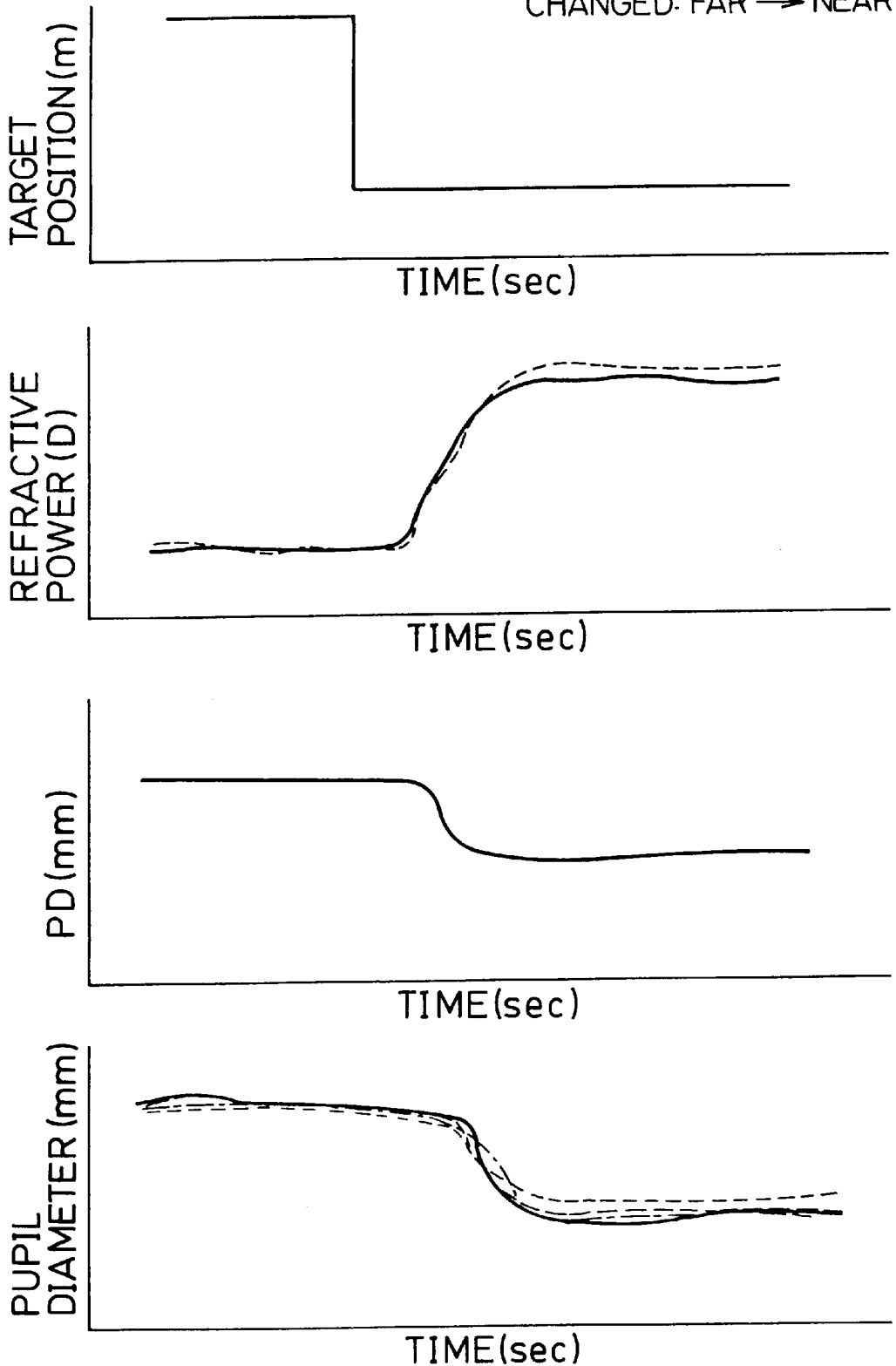
FIG. 26 represents diagrams to show status changes of data such as ocular refractive power of an eye under measurement when a target is instantaneously switched over from "far" to "near"

FIG. 26 shows the changes over time of ocular refractive power, interpupillary distance and pupil diameter when the target is instantaneously changed from the first gaze target 35 to the second gaze target 36 (from "far" to "near").

Figure 27:
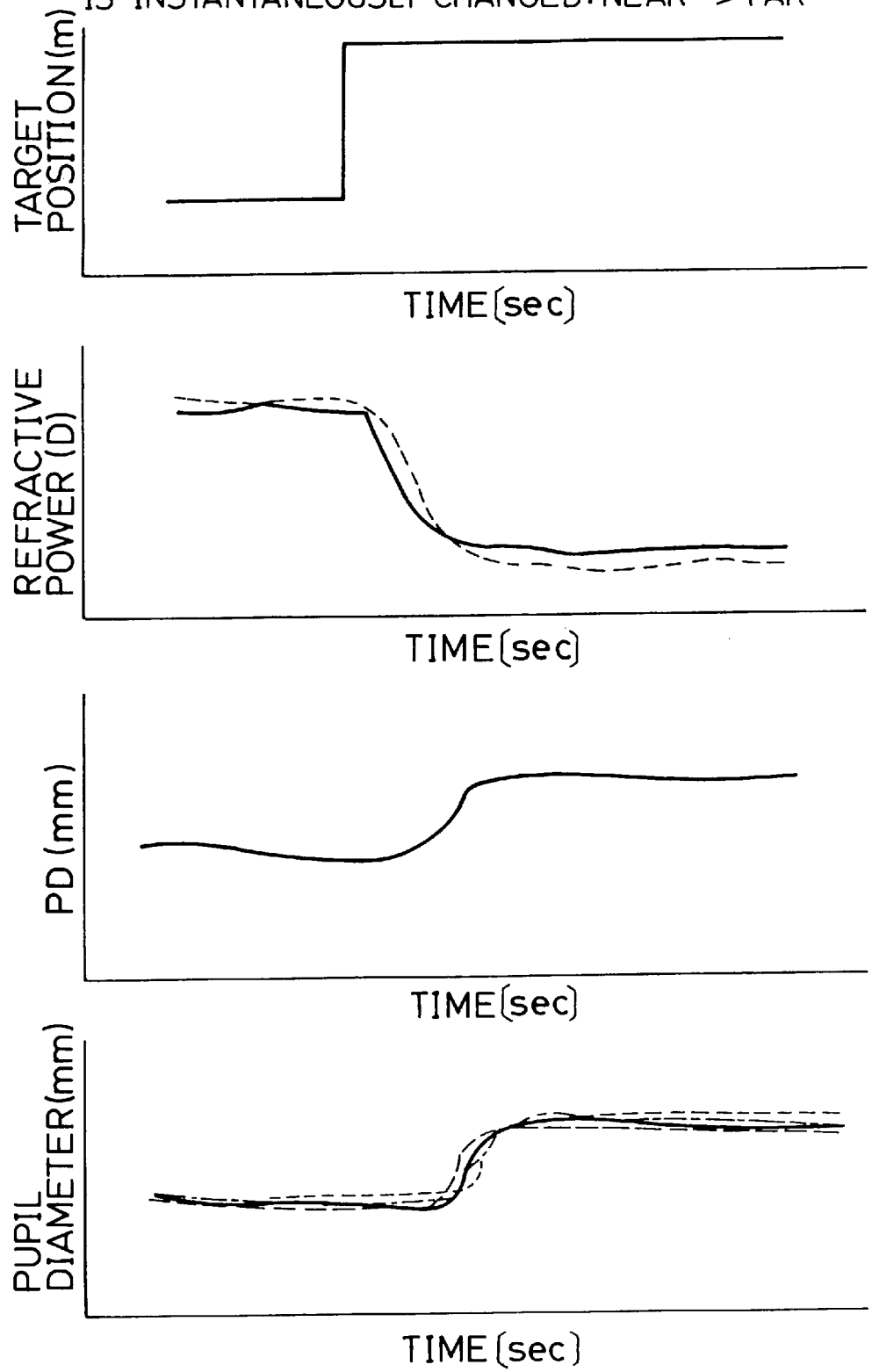
FIG. 27 represents diagrams to show status changes of data such as ocular refractive power of an eye under measurement when a target is instantaneously switched over from "near" to "far"

FIG. 27 shows the changes over time of ocular refractive power, interpupillary distance and pupil diameter when the target is instantaneously changed from the second gaze target 36 to the first gaze target 35 (from "near" to "far").

In both cases, accommodation function of the eyes under measurement is started with some delay from the time of the change of the target position, and final ocular refractive power is reached after a certain fixed time.

There are the following two types of measurement data according to the aspect of target switch-over:

(1) Target change: far→near

Change of target position: When target position is changed from 2.0 m (far) to 0.4 m (near), interpupillary distance is shortened, pupil diameter is decreased, and ocular refractive power is turned to stronger.

(2) Target change: near→far

Change of target position: When the position of the target is changed from 0.4 m (near) to 2.0 m (far), interpupillary distance is turned to longer, pupil diameter is increased, and ocular refractive power is changed to weaker.

Figure 34:
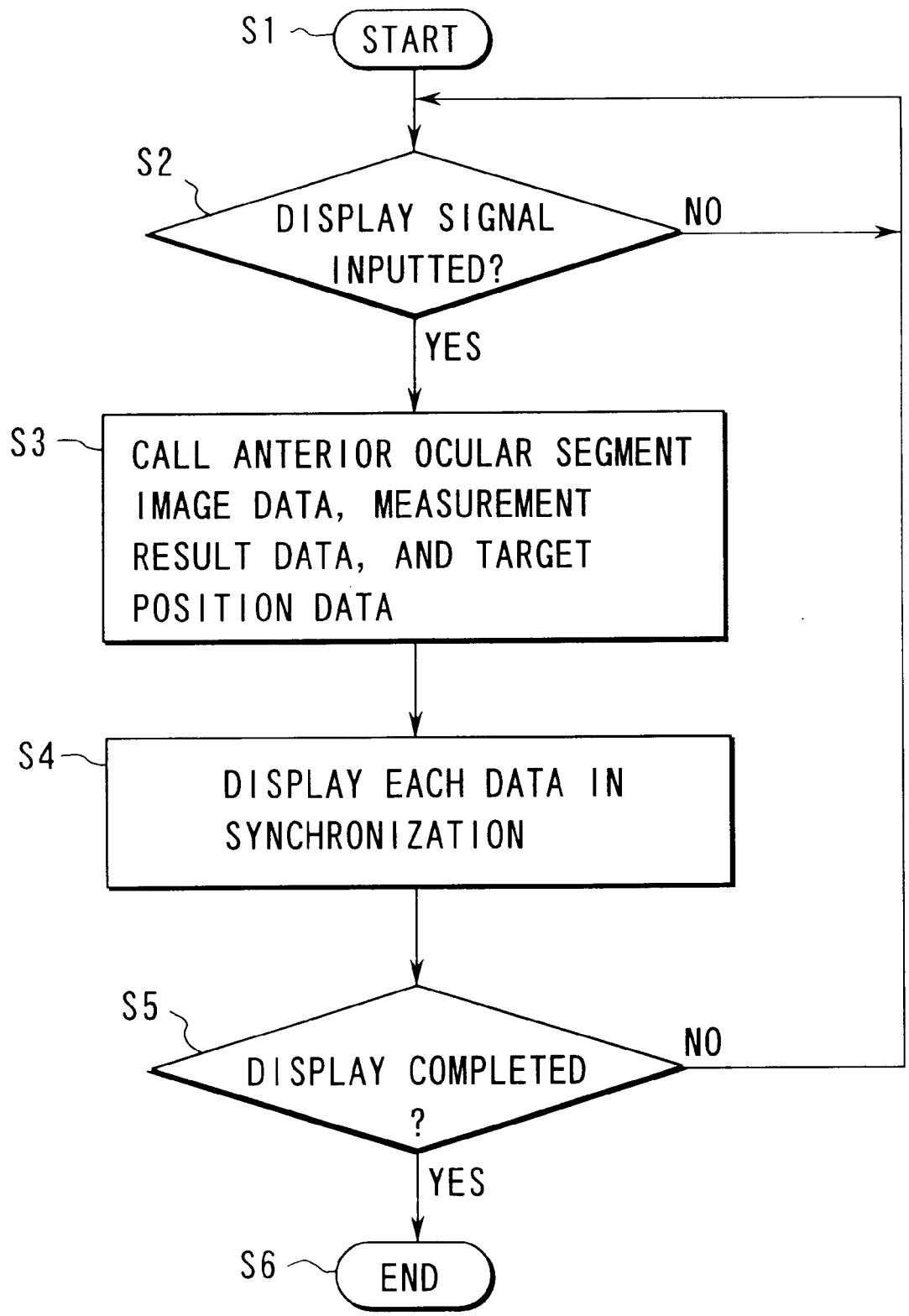
FIG. 34 is a flow chart when data is displayed again.

The anterior ocular segment image data and measurement data thus obtained and stored in the frame memory 16 are processed as shown in FIG. 34 as to be described later and are displayed again over time, and the conditions at the measurement are reproduced.

Figure 28:
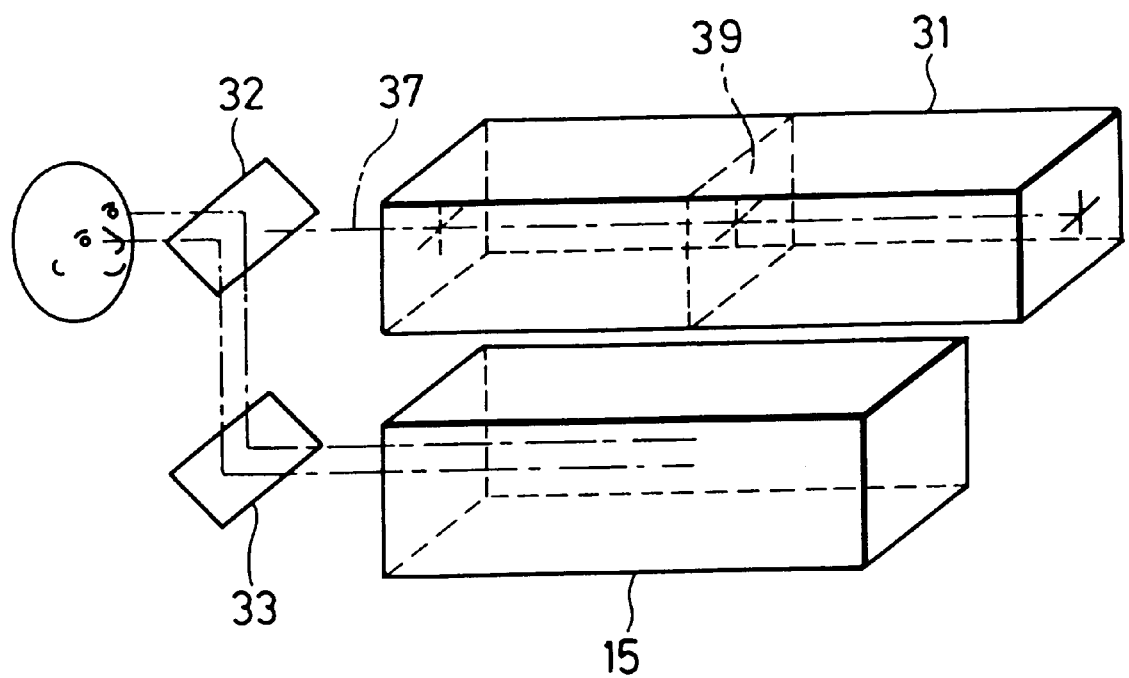
FIG. 28 is a drawing to show general arrangement of a second embodiment of the present invention.

FIG. 28 shows a second embodiment of the present invention. In this embodiment, a target system 31 comprises a movable gaze target 39, which is moved along the transmission light optical axis 37 by a driving unit (not shown), and the driving unit is controlled by the control unit 18. In this embodiment, changes over time of ocular refractive power, interpupillary distance and pupil diameter of the eye under measurement can be measured when the position of the gaze target is continuously changed.

When the measurement starting switch 19, which indicates the start of the measurement, is operated by the examiner, the control unit 18 turns the movable gaze target 39 on, and the position of the movable gaze target 39 is changed by switch operation. Before and after the change of target position and during movement, image signal are sequentially incorporated from the photodetection element 9. By the processing as described above, data for each predetermined time interval of the first predetermined period of the movable gaze target 39, and the data for each predetermined time interval of the second predetermined period (after operation of the switch, during movement of the movable gaze target 39, and after the change of target position) are calculated and are stored in the frame memory 16. The measurement under each of these conditions is displayed at real time on the display unit 14 so that detailed conditions over time can be clearly indicated.

Figure 29:
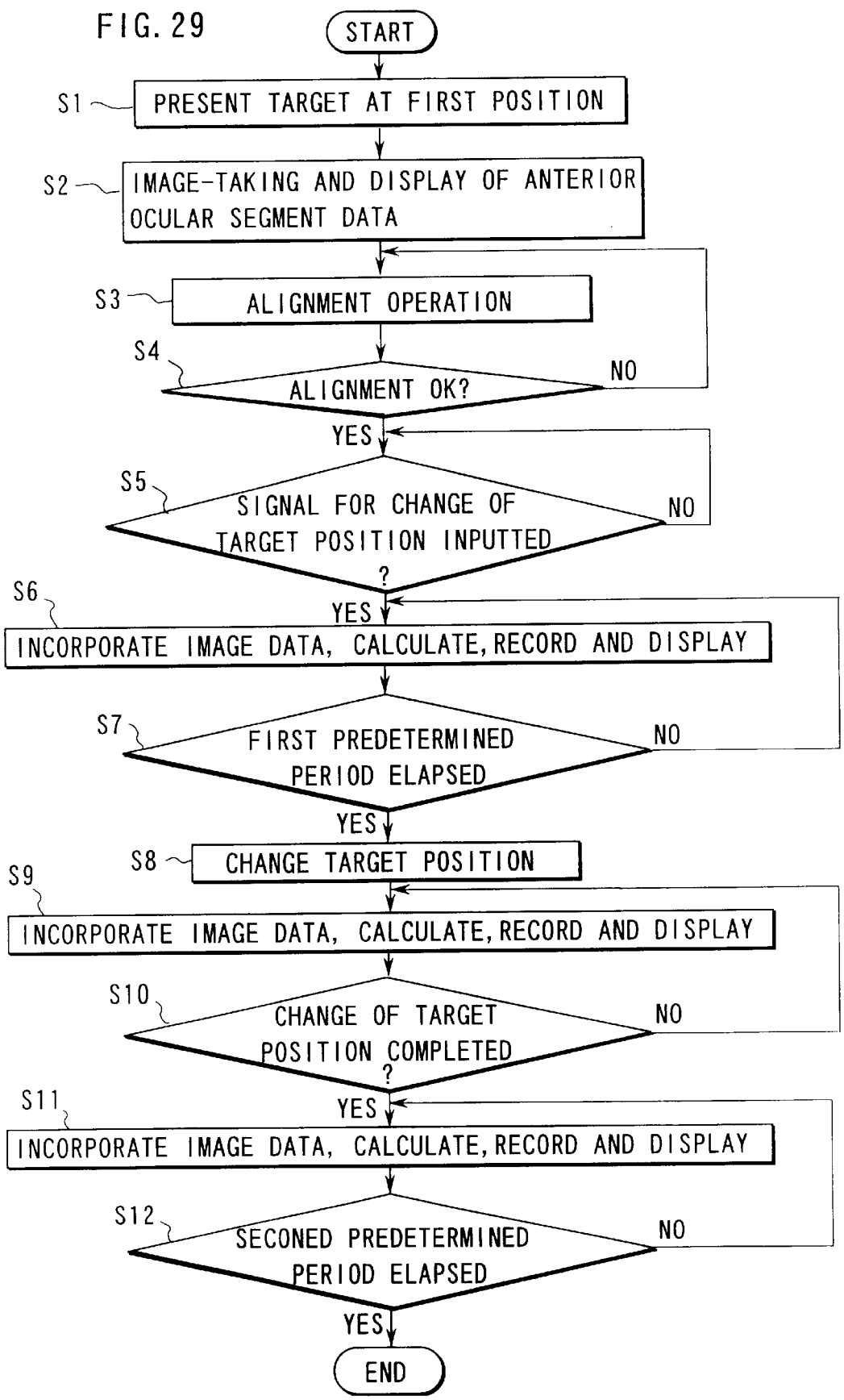
FIG. 29 is a flow chart to show a second measuring method.

One of the measuring methods according to the second embodiment will be described now in connection with FIG. 29.

(Start of Measurement)

S1: The movable gaze target 39 is presented at a first position and at "far" position (e.g. 2 m).

S2: A photodetection signal received on the photodetection element 9 is received by an arithmetic unit 13, and it is stored in the frame memory 16 as anterior ocular segment data including two eyes of the person under measurement in association of the measuring time. Then, the anterior ocular segment image data is displayed on the display unit 14 such as monitor unit.

S3: On the display unit 14, data such as scale for alignment are displayed at the same time, and alignment is performed for the anterior ocular segment image displayed using the scale as a reference.

S4: This alignment procedure is repeated until correct position is reached. When correct position has been reached, it is advanced to S5:

S5: The measurement starting signal which means the change of the target position is turned to an input standby status. When the measurement starting signal is inputted by operation of the measurement starting switch 19, it is advanced to S6.

S6: Image data is incorporated. As shown in FIG. 15, measurement data for the eye to be measured such as ocular refractive power, pupil diameter, interpupillary distance, etc. for both eyes are calculated. The results of calculation are stored in the frame memory 16 in association with the measuring time and are displayed on the display unit (CRT) 14.

S7: It is judged whether the first predetermined period has elapsed or not.

In case the first predetermined period has not elapsed, it is turned back to S6, and image of the anterior ocular segment is incorporated until the first predetermined period elapses, and measurement data are calculated, stored and displayed. When the first predetermined period has elapsed, it is advanced to S8.

S8: The control unit 18 moves the movable gaze target 39 to be indicated from the first position to the second gaze target 36 (the second position (e.g. 0.4 m)). It is advanced to S9.

S9: The image of anterior ocular segment when the movable gaze target 39 is moving is incorporated, and measurement data are calculated, stored and displayed.

S10: It is judged whether movement of the movable gaze target 39 has been completed or not. If it is not completed, it is turned back to S7. Further, image of anterior ocular segment when the movable gaze target 39 is moving is incorporated, and the measurement data are calculated, stored and displayed. When movement is completed, it is advanced to S11.

S11: Image data after moving of the movable gaze target 39 is incorporated, and the measurement data are calculated, stored and displayed.

S12: It is judged whether the second predetermined period has elapsed or not. If the predetermined period has elapsed, the measurement is completed.

Figure 31:
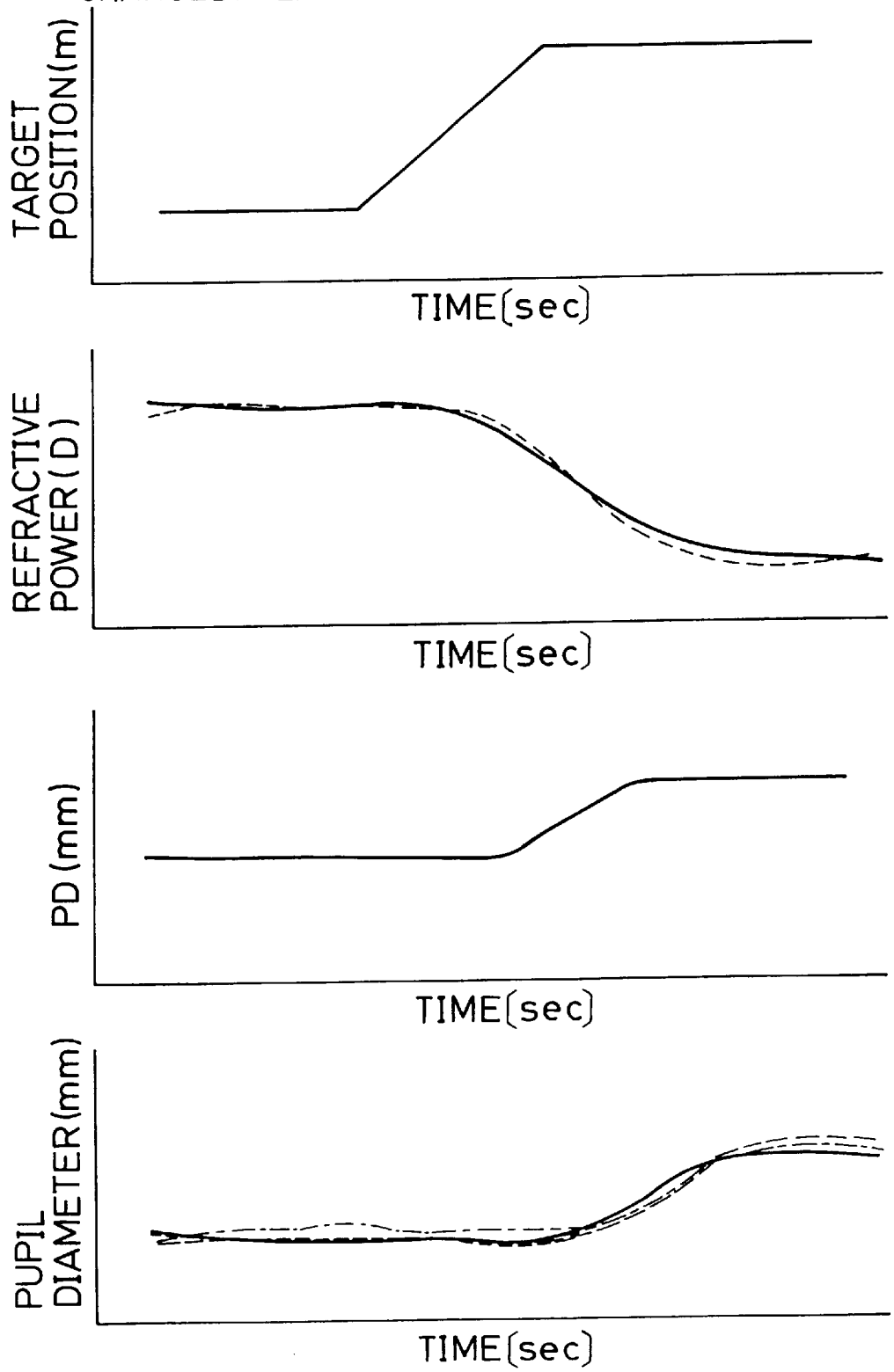
FIG. 31 represents diagrams to show status changes of data such as ocular refractive power of an eye under measurement when the target is gradually moved from "near" to "far"

The following four types of measurement data are obtained according to the aspect of moving of the target:

(1) Change of target: far→near
(2) Change of target: near→far
(3) Moving of target: far→near
(4) Moving of target: near→far FIG. 31 shows the conditions of changes over time of ocular refractive power, interpupillary distance and pupil diameter when the movable gaze target 39 is moved from the first position to the second position.

Figure 32:
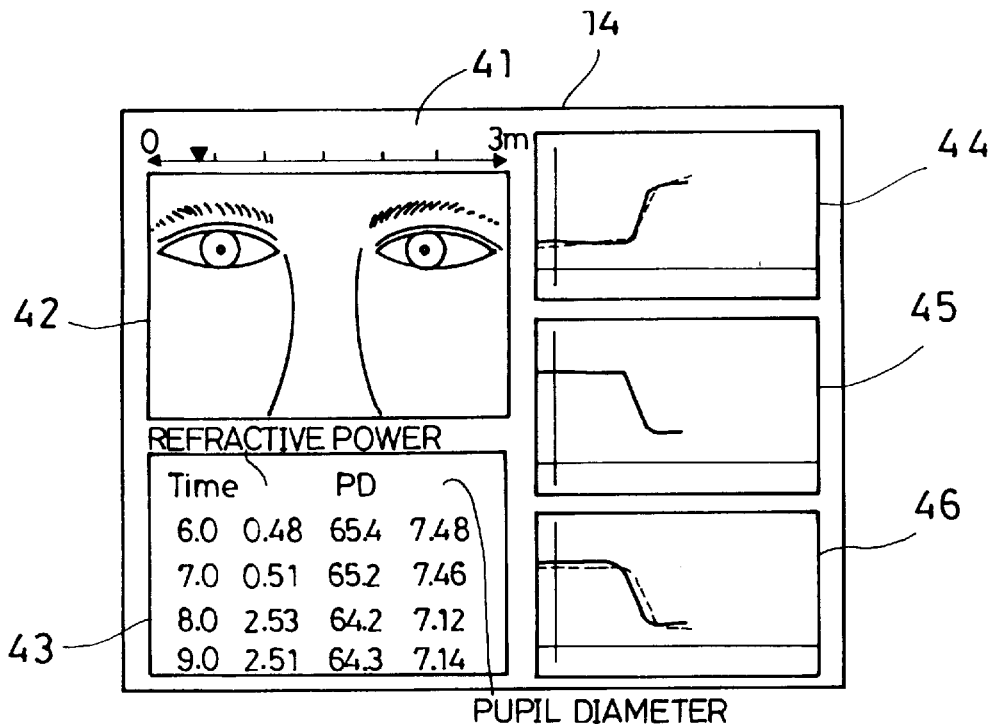
FIG. 32 is a drawing to show an aspect of display in the second embodiment.

FIG. 32 shows the conditions of changes over time of ocular refractive power, interpupillary distance and pupil diameter when the movable gaze target 39 is moved from the second position to the first position.

Figure 33:
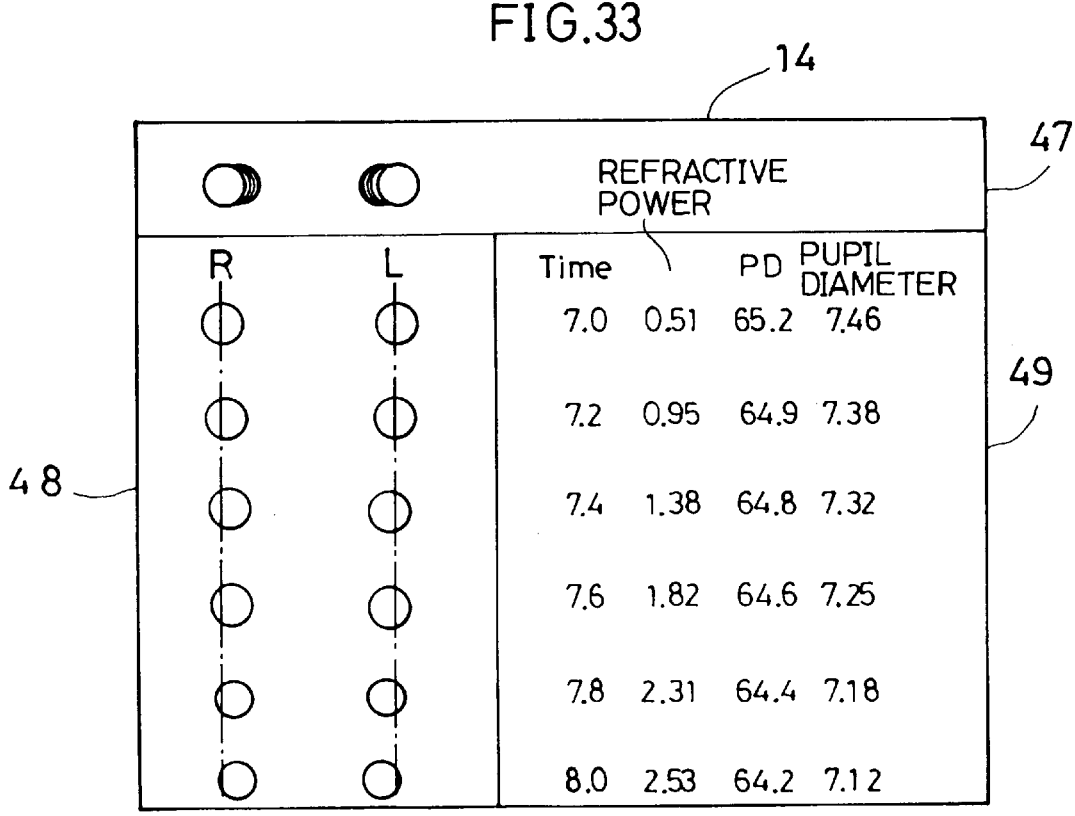
FIG. 33 is a drawing to show an aspect of another display in the second embodiment.

Referring to FIG. 32–FIG. 34, description will be given now on the aspect of display in the second embodiment.

FIG. 32 shows a display screen on the display unit (CRT) 14. A target position display section 41, an anterior ocular segment display section 42, a measured data display section 43, an ocular refractive power display section 44, a PD display section 45, and a pupil diameter display section 46 are displayed on the screen.

The target position display section 41 can indicate at which position the movable gaze target 39 is located at present or whether it is moving or is stopped according to the movement of an inverted triangular arrow mark. By the anterior ocular segment display section 42, the examiner can judge the condition of the anterior ocular segment. A plurality of numerical data under measurement are displayed over time on the measured value display section 43, and the most up-to-date data can be additionally displayed at real time and can be compared with the data in the past. The data indicated on the measured value display section 43 are displayed in graphic representation on the ocular refractive power display section 44, the PD display section 45, and the pupil diameter display section 46, and these correspond to the graphs shown in FIG. 30 and FIG. 31.

FIG. 33 shows another type of display screen of the display unit (CRT) 14. A first pupil display section 47, a second pupil display section 48, and a measured value display section 49 are displayed on the screen.

Pupil images corresponding to the measurement data are displayed in overlapping on the first pupil display section 47, and each pupil image has different color so that the overlapped images can be distinguished from each other. By displaying the images in overlapping, the changes of pupil position under measurement can be visually confirmed. Also, a right pupil standard position R and a left pupil standard position L are displayed in linear arrangement on the screen on the second pupil display section 48, and pupil images corresponding to the measurement data are displayed in overlapping on the right pupil standard position R and the left pupil standard position L over time with the position of each image deviated from each other. FIG. 33 shows an example where the data are sequentially displayed from above. Because pupil images are displayed simultaneously with the right pupil standard position R and the left pupil standard position L, changes of position of the pupil with respect to the standard position can be clearly indicated.

Numerical data under measurement are displayed over time in a plurality of rows on the measured value display section 49, and each of the rows corresponds to the row of the pupil displayed in the second pupil display section 48.

The measurement data can be displayed at real time on the display unit 14, while the data already measured are stored in the frame memory 16, and the data already measured can be displayed at any desired time after measurement. The data are recorded in association with the measuring time. Accordingly, in the display of the data already measured, only the final data can be displayed or a plurality of measurement data can be displayed at the same time, or the data can be displayed over time in the same manner as the display at the time of measurement.

FIG. 34 shows an operation to re-display over time the data, which has been already measured and stored.

When a display instruction is issued, an anterior ocular segment image data, a measurement result data, and a target position data stored in the frame memory 16 are called, and these data are synchronously displayed to align with the course of time. When a series of data have been displayed, re-display is completed.

Figure 35:
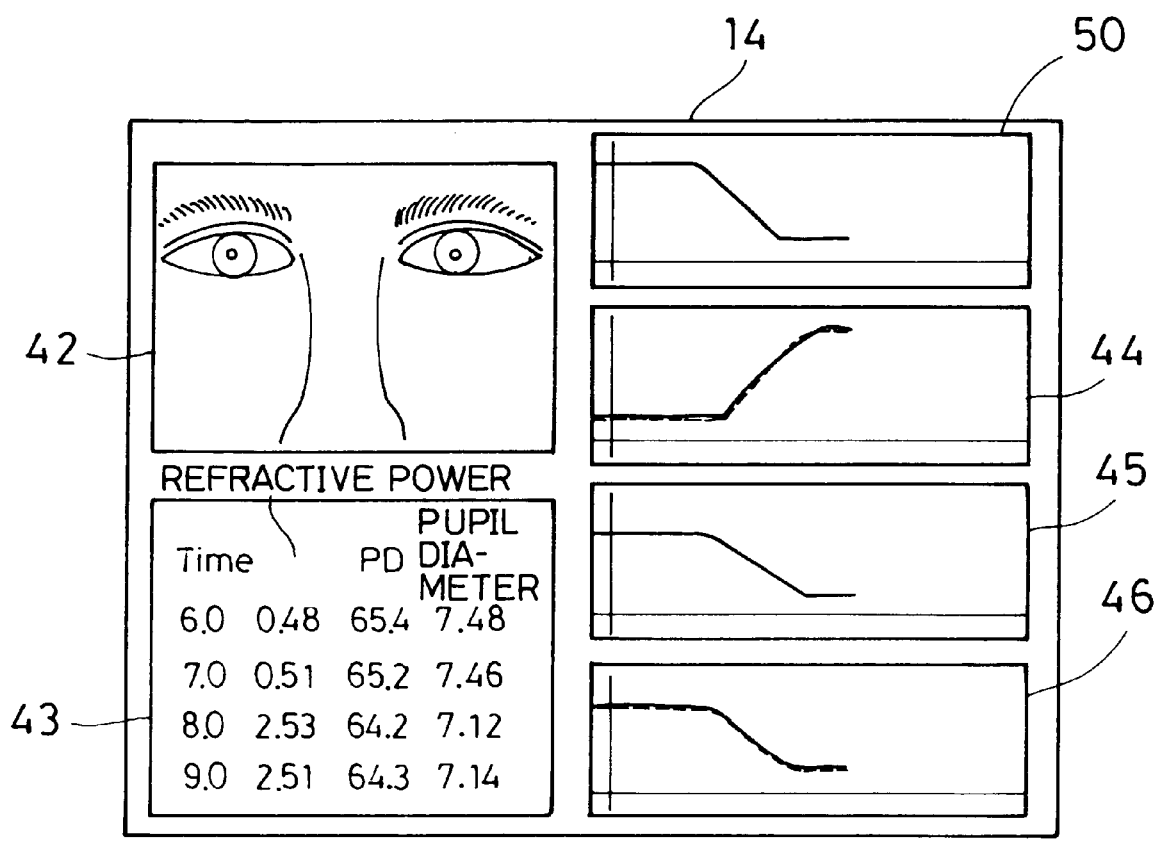
FIG. 35 is a drawing to show still another aspect of display in the second embodiment.

FIG. 35 shows a variation of the display screen of the display unit (CRT) 14 shown in FIG. 32. In FIG. 35, the anterior ocular segment display section 42, the measured value display section 43, the ocular refractive power display section 44, the PD display section 45, and the pupil diameter display section 46 are the same as in FIG. 32, and detailed description is not given here.

Figure 30:
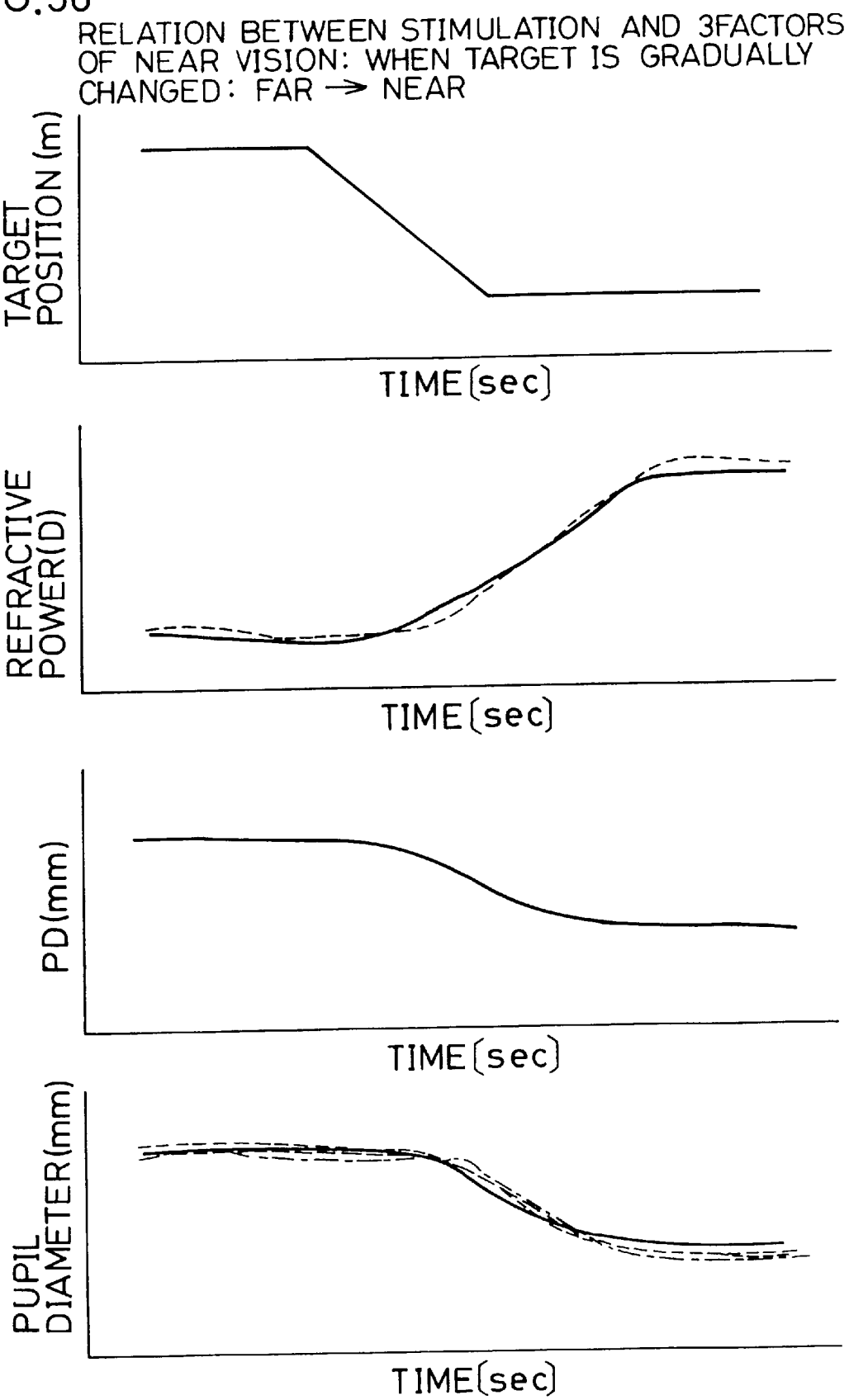
FIG. 30 represents diagrams to show status changes of data such as ocular refractive power of an eye under measurement when the target is gradually moved from "far" to "near"

On this display screen, a target position display section 50 displays the position of the target over time in the same manner as the ocular refractive power display section 44, the PD display section 45, and the pupil diameter display section 46, and these correspond to the graphs shown in FIG. 30 and FIG. 31. On the target position display section 50, the axis of abscissa represents time, and the axis of ordinate represents a distance from the eye under measurement to the target. In the figure, the condition where the target is moved closer is shown. By the target position display section 50, it is possible to detect the change of target position over time. By indicating the data over time as the other display sections such as the ocular refractive power display section 44, the PD display section 45, and the pupil diameter display section 46, changes of ocular refractive power, PD, and pupil diameter corresponding to the changes of target position can be visually and easily recognized.

In the above embodiment, description has been given on the measurement when the eye under measurement gazes at the target, while it is needless to say that it may be the measurement when the eye under measurement is watching not the target but scenery in the distance, i.e. when the eye is in the state of natural vision.

As described above, according to the present invention, three factors of ocular refractive power, pupil diameter and interpupillary distance can be measured at the same time. Also, changes over time of one or all of these three factors of the eye under measurement when target position is changed can be measured at real time. Further, measurement data can be displayed over time and at real time. Thus, the examiner can instantaneously identify the results of measurement and can visually recognize again the conditions of the desired pupil image.

What is claimed is:

1. An ophthalmologic measuring system, comprising a light source unit for emitting an illuminating light beam for illuminating a fundus of each of both eyes of a person under measurement, a projection optical system for projecting said illuminating light beam from said light source unit to said fundus of each of said eyes of the person under measurement, a photodetection optical system including a light blocking member which blocks a part of a reflection light beam coming from said fundus of said eye of the person under measurement and is arranged in an optical path and at approximately conjugate position to a pupil of said eye under measurement so that change occurs in light amount distribution depending on ocular refractive power, a photodetection unit arranged at approximately conjugate position to a pupil of said eye under measurement and receives photodetection light beam from said photodetection optical system, a storage unit for storing a photodetection signal of said photodetection unit, a control arithmetic unit for obtaining at least one of interpupillary distances, ocular refractive powers and pupil diameters of said eye under measurement based on said photodetection signal of said photodetection unit, and a display unit for displaying an anterior ocular segment image of said eye under measurement during measurement period and for displaying over time and at real time data of interpupillary distance, ocular refractive power and pupil diameter of said eye under measurement, which are results of measurement during measurement period.

2. An ophthalmologic measuring system according to claim 1, wherein said system further comprises a target system for showing a target to said person under measurement by changing the target position from a first target position to a second target position different from said first target position in response to operation by a measuring person, wherein said control arithmetic unit determines at least one of interpupillary distances, ocular refractive powers and pupil diameters of said eye under measurement before and after change of said target positions based on said photodetection signals of said photodetection unit obtained before and after said change of said target position by said target system.

3. An ophthalmologic measuring system according to claim 2, wherein said system comprises a storage unit for storing an anterior ocular segment signal from said photodetection unit, and an anterior ocular segment image of said eye under measurement is displayed on said display unit with delay of time as required for arithmetic processing at said control arithmetic unit based on said signal stored in said storage unit, and said anterior ocular segment image when said target position is changed and results of the measurement are displayed at real time.

4. An ophthalmologic measuring system, comprising a light source unit for emitting an illuminating light beam for illuminating a fundus of each of both eyes of a person under measurement, a projection optical system for projecting said illuminating light beam from said light source unit to said fundus of each of said eyes of the person under measurement, a photodetection optical system including a light blocking member which blocks a part of a reflection light beam coming from said fundus of said eye of said person under measurement and is arranged in an optical path and at approximately conjugate position to a pupil of said eye under measurement so that change occurs in light amount distribution depending on ocular refractive power, a photodetection unit arranged at approximately conjugate position to a pupil of said eye under measurement and receives photodetection light beam from said photodetection optical system, a storage unit for storing a photodetection signal of said photodetection unit, a target system for showing a target to said person under measurement by changing target position from a first target position to a second target position different from said first target position, a control arithmetic unit for obtaining interpupillary distances, ocular refractive powers and pupil diameters of said eye under measurement before and after change of said target position based on said photodetection signals of said photodetection unit obtained before and after change of said target position by said target system, a storage unit for storing an anterior ocular segment signal of said photodetection unit and results of calculation by said control arithmetic unit in association with movement of said target by said target system, and a display unit for displaying an anterior ocular segment of said photodetection unit and said results of calculation by said control arithmetic unit in association with said movement of said target by said target system based on the anterior ocular segment signal stored in said storage unit and said results of said calculation.

5. An ophthalmologic measuring system according to claim 4, wherein said display unit aligns and displays pupil images in association with said movement of said target by said target system so that movement of pupils of said eye under measurement on said photodetection unit can be sequentially identified.

6. An ophthalmologic measuring system according to claim 5, wherein pupil images are partially overlapped each other or are displayed in different colors.

7. An ophthalmologic measuring system according to claim 2 or 4, wherein said display unit is designed in such manner that movement of said target system can be visually identified.

* * * * *